US011983884B2

(12) United States Patent
Giannini et al.

(10) Patent No.: US 11,983,884 B2
(45) Date of Patent: May 14, 2024

(54) TUMORAL MASS DETECTION SYSTEM BASED ON MAGNETIC RESONANCE IMAGING

(71) Applicants: UNIVERSITA' DEGLI STUDI DI TORINO, Turin (IT); FONDAZIONE DEL PIEMONTE PER L'ONCOLOGIA, Candiolo (IT)

(72) Inventors: Valentina Giannini, Turin (IT); Simone Mazzetti, Turin (IT); Daniele Regge, Turin (IT)

(73) Assignees: UNIVERSITA' DEGLI STUDI DI TORINO, Turin (IT); FONDAZIONE DEL PIEMONTE PER L'ONCOLOGIA, Candiolo (IT)

( * ) Notice: Subject to any disclaimer, the term of this patent is extended or adjusted under 35 U.S.C. 154(b) by 754 days.

(21) Appl. No.: 17/052,941

(22) PCT Filed: May 8, 2019

(86) PCT No.: PCT/IB2019/053783
§ 371 (c)(1),
(2) Date: Nov. 4, 2020

(87) PCT Pub. No.: WO2019/215637
PCT Pub. Date: Nov. 14, 2019

(65) Prior Publication Data
US 2021/0219861 A1      Jul. 22, 2021

(30) Foreign Application Priority Data
May 8, 2018  (IT) .................. 102018000005163

(51) Int. Cl.
*A61B 5/00*    (2006.01)
*A61B 5/055*   (2006.01)
(Continued)

(52) U.S. Cl.
CPC .............. *G06T 7/143* (2017.01); *A61B 5/055* (2013.01); *A61B 5/7264* (2013.01);
(Continued)

(58) Field of Classification Search
CPC .............................. A61B 5/055; A61B 5/7264
See application file for complete search history.

(56) References Cited

U.S. PATENT DOCUMENTS

2008/0125643 A1    5/2008  Huisman et al.
2018/0082153 A1*   3/2018  Wan .................... G06T 7/0014

FOREIGN PATENT DOCUMENTS

EP        3 081 955         10/2016
WO    WO 2013/086026         6/2013
(Continued)

OTHER PUBLICATIONS

Giannini V., Mazzetti S., Regge D. et al., "A fully automatic computer aided diagnosis system for peripheral zone prostate cancer detection using multi-parametric magnetic resonance imaging", Computerized Medical Imaging and Graphics Sep. 25, 2015; 46:219-226.

*Primary Examiner* — Joel F Brutus
(74) *Attorney, Agent, or Firm* — Leason Ellis LLP

(57) ABSTRACT

A system for detecting tumoral masses in an unknown tissue is described, that can be coupled to an MRI system for receiving a number of unknown tissue scans, each scan comprising a corresponding plurality of MRI images relating to a group of voxels, each voxel being associated with a corresponding portion of unknown tissue, the MRI images of each scan being indicative of values of at least a corresponding initial parameter. The detection system determines for each voxel a corresponding probability value, indicative of the probability of the corresponding portion of unknown tissue including a corresponding tumoral portion. Furthermore, the detection system determines, for a plurality of
(Continued)

voxel groups, a corresponding group aggressiveness value, indicative of the aggressiveness of the tumoral mass formed by the tumoral portions present in the corresponding portions of unknown tissue.

14 Claims, 18 Drawing Sheets

(51) Int. Cl.
    *G06F 18/20*     (2023.01)
    *G06T 7/143*     (2017.01)
    *G06V 20/69*     (2022.01)
    *G16H 30/40*     (2018.01)
    *G16H 50/20*     (2018.01)

(52) U.S. Cl.
    CPC .......... *G06F 18/285* (2023.01); *G06V 20/698* (2022.01); *G16H 30/40* (2018.01); *G16H 50/20* (2018.01); *A61B 2576/00* (2013.01)

(56) References Cited

FOREIGN PATENT DOCUMENTS

| WO | WO 2014/174317 | 10/2014 |
| WO | WO 2017/165801 | 9/2017 |

\* cited by examiner $$
\begin{array}{c}
\phantom{XX} \overbrace{\phantom{XXXXXXXXXXXX}}^{J} \\
\phantom{XX} P_1 \phantom{XX} P_2 \phantom{XXX} P_J \phantom{XXX} P_S
\end{array}
$$

PATIENT 1

$$
\begin{array}{c}
V(1,1,1) \\
V(1,1,2) \\
\vdots \\
V(M,M,N)
\end{array}
\left(
\begin{array}{cccc}
P_1^{1,1} & P_2^{1,1} & \cdots & P_J^{1,1} \\
P_1^{2,1} & P_2^{2,1} & \cdots & P_J^{2,1} \\
\vdots & \vdots & & \vdots \\
P_1^{N,1} & P_2^{N,1} & \cdots & P_J^{N,1}
\end{array}
\right)
\left(
\begin{array}{c}
0 \\
1 \\
\vdots \\
1
\end{array}
\right)
$$

PATIENT 2

$$
\begin{array}{c}
V(1,1,1) \\
V(1,1,2) \\
\vdots \\
V(M,M,N)
\end{array}
\left(
\begin{array}{cccc}
P_1^{1,2} & P_2^{1,2} & \cdots & P_J^{1,2} \\
P_1^{2,2} & P_2^{2,2} & \cdots & P_J^{2,2} \\
\vdots & \vdots & & \vdots \\
P_1^{N,2} & P_2^{N,2} & \cdots & P_J^{N,2}
\end{array}
\right)
\left(
\begin{array}{c}
1 \\
0 \\
\vdots \\
0
\end{array}
\right)
$$

300    310

$\vdots$

PATIENT Q $$
\begin{array}{c}
V(1,1,1) \\
V(1,1,2) \\
\vdots \\
V(M,M,N)
\end{array}
\left(
\begin{array}{cccc}
P_1^{1,Q} & P_2^{1,Q} & \cdots & P_J^{1,Q} \\
P_1^{2,Q} & P_2^{2,Q} & \cdots & P_J^{2,Q} \\
\vdots & \vdots & & \vdots \\
P_1^{N,Q} & P_2^{N,Q} & \cdots & P_J^{N,Q}
\end{array}
\right)
\left(
\begin{array}{c}
1 \\
1 \\
\vdots \\
0
\end{array}
\right)
$$

$\rightarrow ROC_t \leftarrow$

FIG. 8

TUMORAL MASS DETECTION SYSTEM BASED ON MAGNETIC RESONANCE IMAGING

CROSS-REFERENCE TO RELATED APPLICATIONS

This patent application is a U.S. National Phase Application under 35 U.S.C. § 371 of International Patent Application No. PCT/IB2019/053783, filed on May 8, 2019, which claims priority from Italian patent application no. 102018000005163, filed on May 8, 2018, all of which are incorporated, as if expressly set forth in their respective entireties herein.

TECHNICAL FIELD

The present invention concerns a tumoral mass detection system based on magnetic resonance imaging (MRI).

BACKGROUND ART

As is known, the diagnosis of tumoral masses, in particular in the case of tumoral masses in the prostate, has various criticalities such as, for example, low sensitivity and specificity of the screening and diagnosis methods. These criticalities negatively affect the patient quality of life and cause an increase in costs for the national health system.

Typically, in order to identify patients in which the presence of a significant prostate tumour is suspected, the so-called PSA (Prostatic Specific Antigen) test is carried out, which evaluates blood PSA levels in the patient under examination. If the PSA values are high, the patient undergoes a prostate biopsy.

Unfortunately, the PSA test has a low specificity and low sensitivity (~30%); this means that approximately 60% of patients with high PSA values, but who do not present significant tumoral masses, are subjected to unnecessary prostate biopsy, undergoing the side effects connected with this operation. On the other hand, patients with potentially serious tumours do not undergo prostate biopsy due to the low levels of PSA detected.

In addition, the prostate biopsy, performed by means of random bioptic sampling, is not always able to provide a complete representation of the tumoral masses. It is known, in fact, that the concordance between the aggressiveness of the tumour at the time of the prostate biopsy and post-biopsy varies between 28% and 69%. In other words, this means that very aggressive tumours can be evaluated as non-aggressive and, consequently, can be under-treated; similarly, patients with non-aggressive tumours can be subjected to radical treatments (i.e. they can be over-treated) when, on the contrary, they could benefit from less invasive treatments with fewer side effects.

In recent times, the use of MRI systems has acquired increasing importance in the management of prostate tumour patients, since these systems have a high sensitivity and a high specificity in identifying clinically significant prostate tumours. However, the diffusion of MRI systems for analysis of prostate tumours is limited by factors such as, for example, the complexity of the examination, the considerable length of the reporting process and dependence on the abilities of the operator (namely the radiologist). In fact, it is necessary to analyse a large volume of images in order to produce an accurate report on the presence and nature of the possible tumoral masses.

In addition, the current MRI systems extract a certain number of parameters, starting from MRI images previously acquired, and subsequently determine the presence or absence of tumoral masses on the basis of said parameters. The Applicant has observed that, although the MRI systems represent an undoubted step forward with respect to previous diagnostic techniques, the diagnostic precision provided by them is still subject to improvement.

DISCLOSURE OF INVENTION

The object of the present invention is therefore to provide a detection system based on MRI images which allows improvement in the precision of the diagnosis of tumoral masses.

According to the present invention, a detection system for detecting tumoral masses is provided, as defined in the attached claims.

BRIEF DESCRIPTION OF THE DRAWINGS

For a better understanding of the present invention a preferred embodiment is now described, purely by way of non-limiting example, with reference to the attached drawings, in which:

FIG. 8 shows matrixes of parameter values acquired used during a curve trend determination step performed by the present detection system;

BEST MODE FOR CARRYING OUT THE INVENTION

Figure 1:
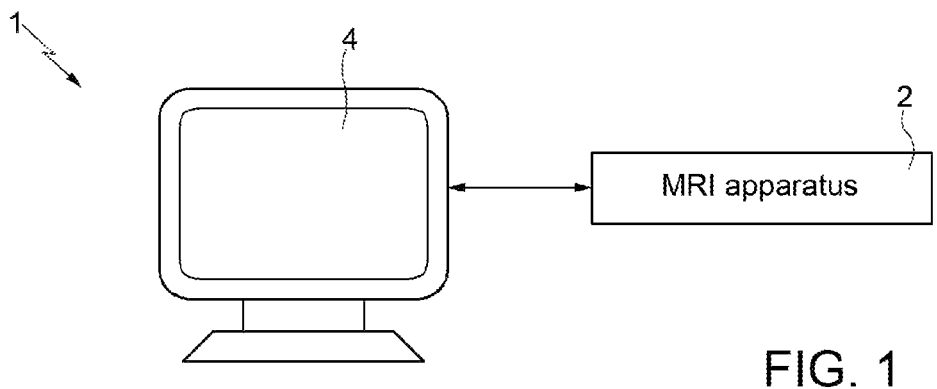
FIG. 1 shows a block diagram of the present detection system.

FIG. 1 shows a system 1, which comprises an MRI apparatus 2, of a known type, and a processing system 4, which are electrically coupled to each other.

As explained below, the system 1 is an image processing system and a diagnostic aid, of computer-assisted type, therefore it is referred to below as CAD system 1.

Below, the CAD system 1 is described with reference to the article "A fully automatic computer aided diagnosis system for peripheral zone prostate cancer detection using multi-parametric magnetic resonance imaging" (Giannini V., Mazzetti S., Regge D. et al., Computerized Medical Imaging and Graphics 2015; 46:219-226), highlighting the differences of the present CAD system 1.

Furthermore, in a first step, the CAD system 1 operates on a selected population of sample patients (for example, including Q sample patients), who have previously undergone radical prostatectomy; in this way, it is possible to know a priori the bioptic result relative to the presence of a prostate tumour, so as to allow a sort of preliminary calibration of the CAD system 1.

Figure 2A:
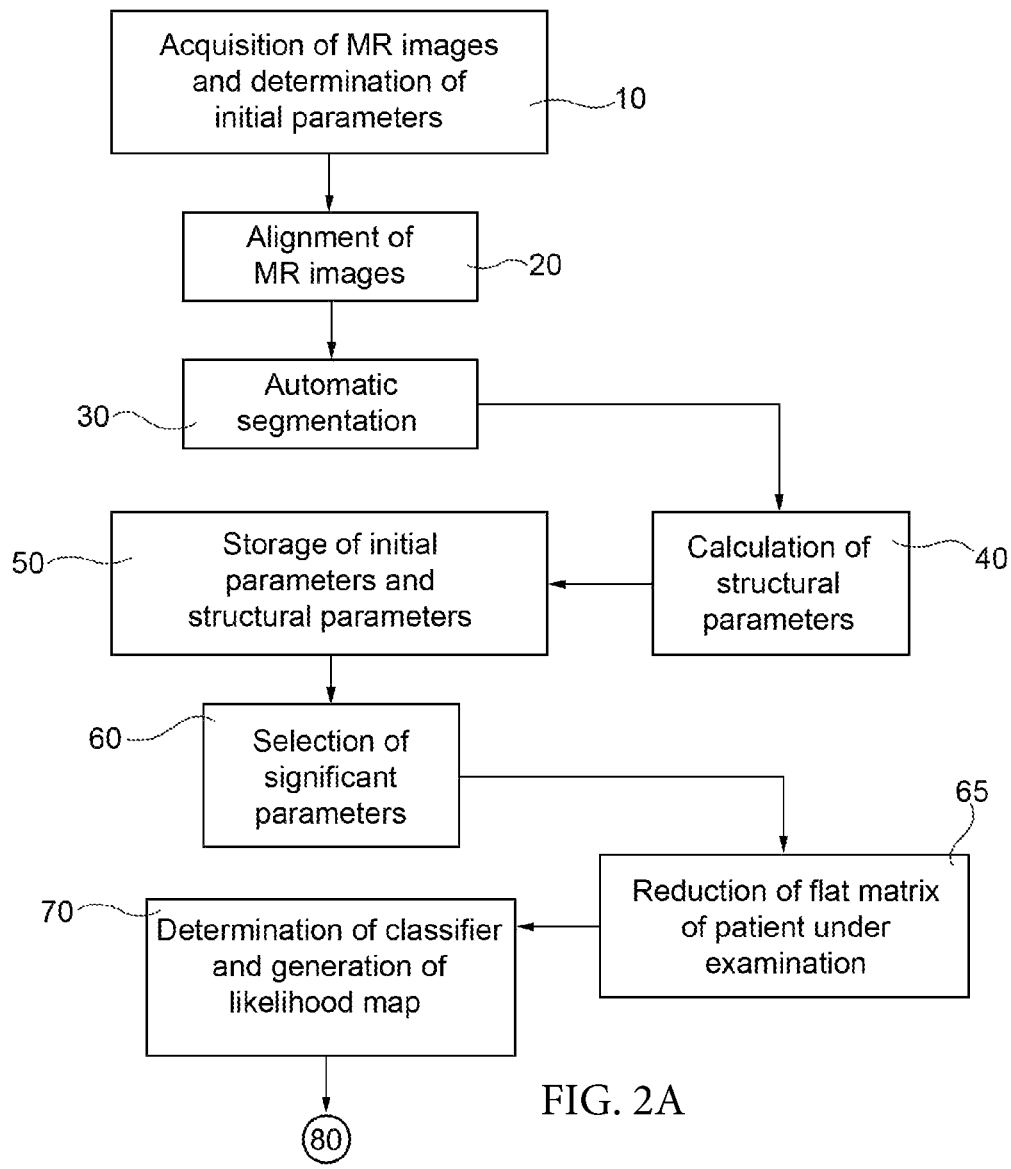
FIGS. 2A-2C, 6, 15 and 21 show flow diagrams relative to operations carried out by the present detection system.
Figure 2B:
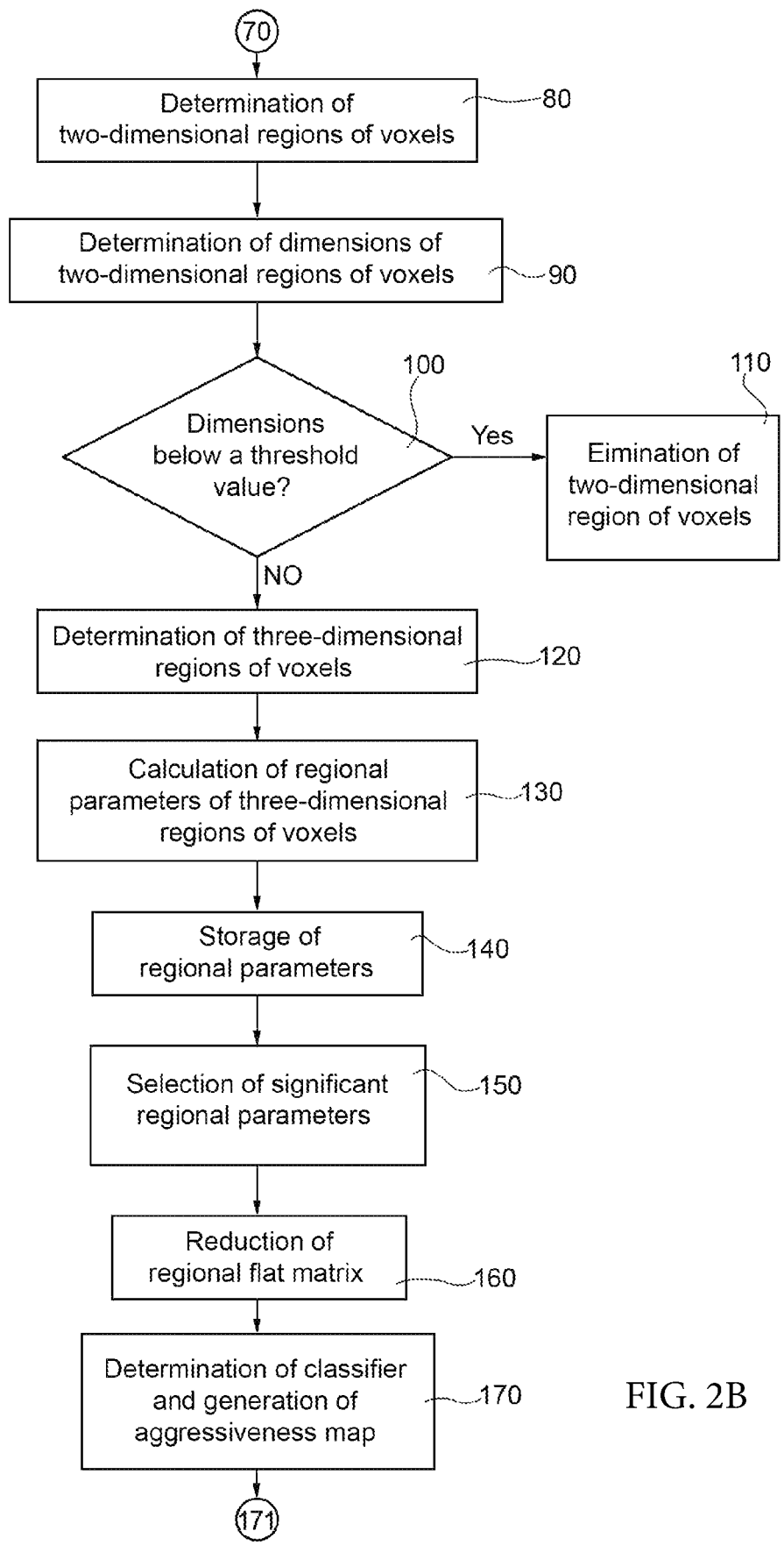
Figure 2C:
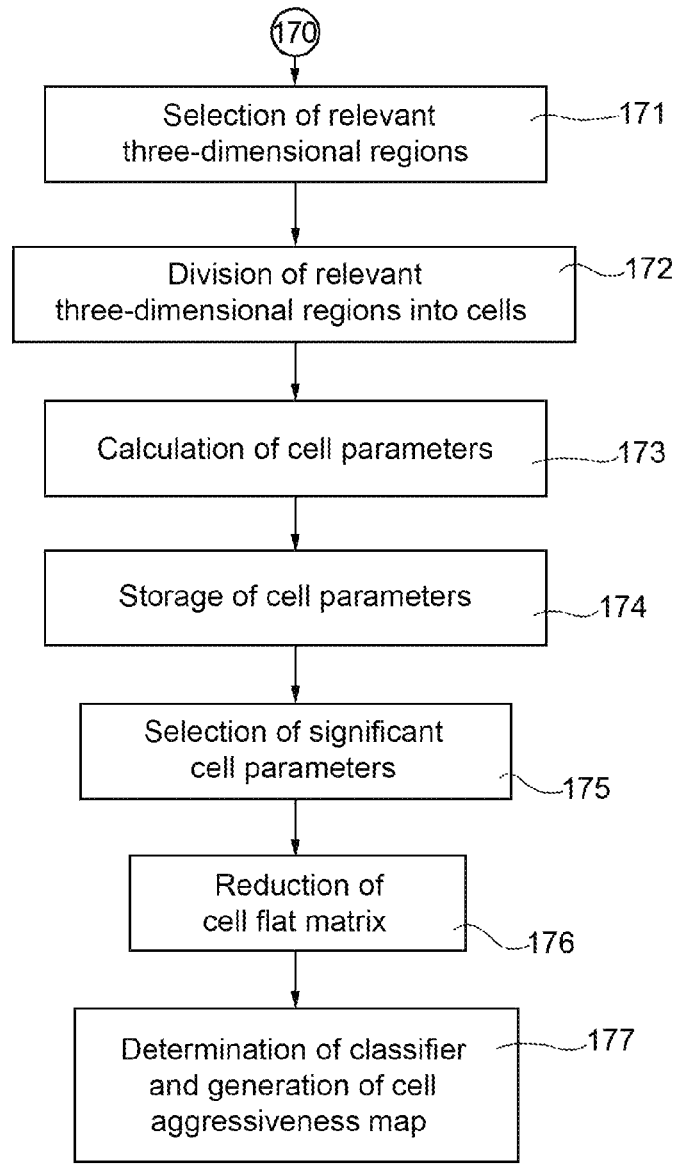

In detail, as shown in FIGS. 2A-2C, for each sample patient, the MRI apparatus 2 acquires (block 10) a plurality of MRI type images, using different image acquisition techniques. In particular, the MRI apparatus 2 uses MRI acquisition techniques to perform scans based on the following image types:

T2 weighted images (abbreviated to "T2w"), which are indicative of a first relaxation time T2 of the tissues analysed by means of a radio frequency (RF) excitation;

diffusion weighted images (DWI), which are indicative of the Brownian motion of the water molecules in different portions of the tissue analysed, and from which images of maps of an apparent diffusion coefficient (ADC) are obtained by means of known logarithmic relations; and images representing dynamic sequences with injection of contrast medium (DCE-MR, Dynamic Contrast-Enhanced Magnetic Resonance), indicative of a second relaxation time T1 induced by the bolus of contrast liquid based on, for example, gadolinium.

In order to acquire the above-mentioned images, the MRI apparatus 2 includes known instruments such as, for example, a scanner using a first coil, having four or more channels in phase (four-channel phased-array), in combination with a second coil, of endorectal type and arranged in the vicinity of the prostate.

Figure 3:
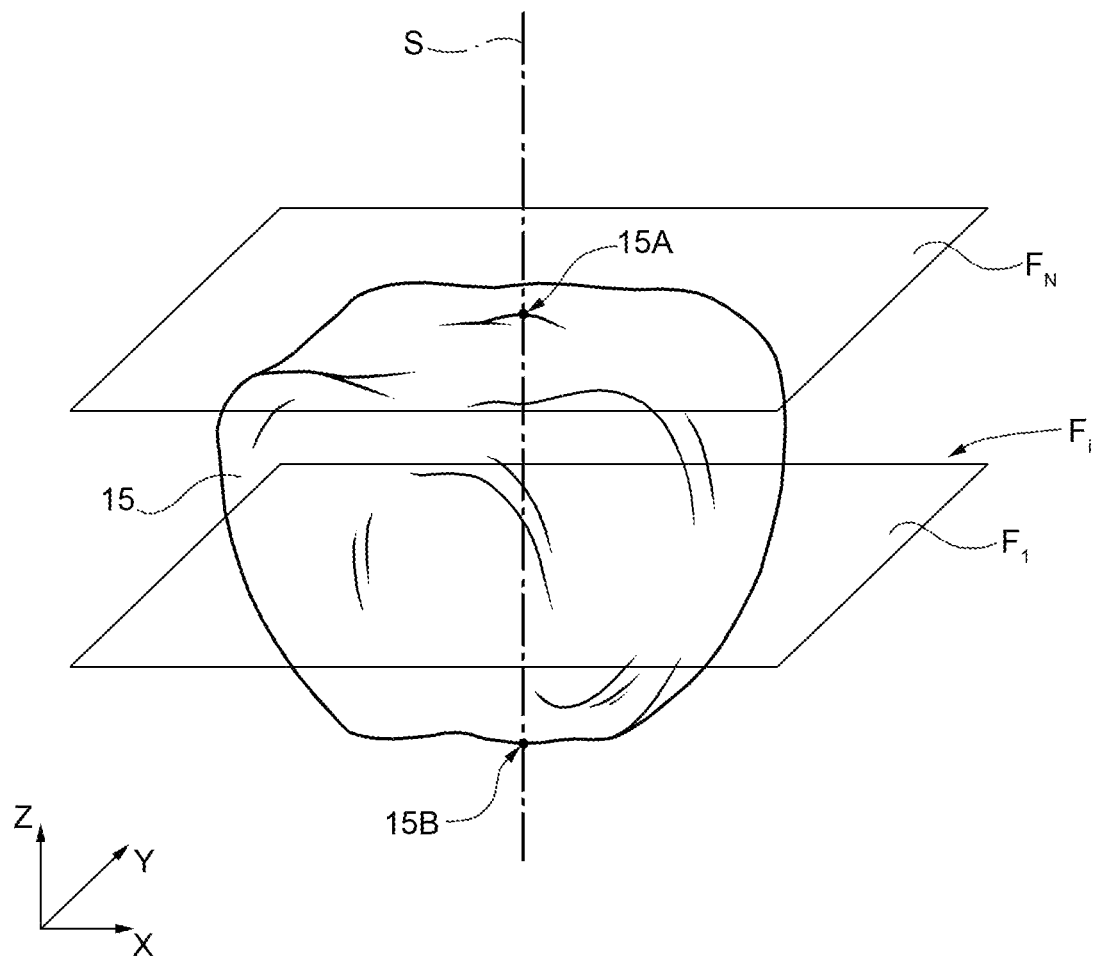
FIG. 3 shows a schematized perspective view of a prostate, during an operative step performed by the present detection system.

In this regard, FIG. 3 shows, in a simplified manner, how any one of the previously mentioned scans is performed. In particular, FIG. 3 schematically shows a prostate 15 of any sample patient, having a base 15A and an apex 15B, crossed by a sagittal axis S, which ideally connects the base 15A to the apex 15B; furthermore, the sagittal axis S is parallel to a first axis Z of a Cartesian reference system XYZ and is perpendicular to planes parallel to a plane XY of the same Cartesian reference system XYZ.

Initially, the MRI apparatus 2 scans the prostate 15, so as to generate a plurality of axial slices (two shown in FIG. 3), indicated overall by the reference notation $F_i$; in detail, i is an integer index with value between 1 and N, where N is the number of axial slices $F_i$ used to perform the section scan of the prostate 15. Furthermore, each axial slice $F_i$ is parallel to the plane XY of the Cartesian reference system XYZ and is, therefore, perpendicular to the sagittal axis S of the prostate 15.

In practice, for each axial slice $F_i$, the MRI apparatus 2 generates a corresponding image; in turn, each image is formed by a corresponding plurality of minimum image units, defined as voxels. In particular, each voxel is representative of a corresponding slice portion of prostatic tissue; in this regard, the above-mentioned slices have thickness, for example, of three millimetres.

The processing system 4 receives and stores the images generated by the MRI apparatus 2, if necessary, after storing the images in a database of the MRI apparatus 2. Furthermore, according to the MRI acquisition technique considered, the images of the corresponding scan are processed in a different manner by the processing system 4.

In particular, the T2w acquisition technique allows N morphological images of the prostate 15 to be acquired relative to the same instant of time t*, so as to allow observation of the variations of the first relaxation time T2 between the axial slices $F_i$.

Analogously, the DWI acquisition technique allows morphological images of the prostate 15 to be acquired, relative to the same instant of time t. More precisely, the DWI acquisition technique acquires at least two corresponding groups of N images each so that, in a first approximation, both are relative to the above-mentioned instant of time t and allow determination, based on said at least two groups, of N images relative to the above-mentioned coefficient ADC. Below, when referring to the DWI N images, reference to the N images relative to the ADC parameter is understood, unless specified otherwise.

On the other hand, according to the DCE-MRI acquisition technique, it is possible to acquire N images of the prostate for each of k instants of time, equally spaced from one another. In particular, the acquisition is performed starting from an initial instant of time $t_0'$ and terminates at a final instant of time $t'_{k-1}$; furthermore, in each instant of time of the time interval $t_0'-t'_{k-1}$ N functional images of the prostate 15 are acquired. Between any two successive instants of time, a period, for example of thirteen seconds, elapses.

In other words, the DCE-MRI acquisition technique allows spatial and temporal acquisition of the images, so that at the end of the acquisition process, we have k·N images of the prostate 15. Furthermore, starting from the acquired images, it is possible to trace, for each voxel, a corresponding time evolution curve, which is defined as contrast uptake curve; in detail, the contrast uptake curve is formed by k corresponding points and is indicative of the time evolution of the distribution of the contrast medium in the corresponding tissue portion of the prostate 15.

Subsequently, the DCE-MRI acquisition technique associates each voxel with one or more parameters indicative of the corresponding contrast uptake curve.

For example, the parameters indicative of the contrast uptake curve may be semi-quantitative or quantitative. The semi-quantitative parameters are calculated starting from the values of the contrast uptake curve and are, for example, maximum absorption (maximum uptake, MU), peak time (time to peak, TTP), the wash-in rate and the washout rate. The quantitative parameters, on the other hand, are obtained by interpolating, for each voxel, the corresponding contrast uptake curve according to two categories of interpolation models; in the case presented, the interpolation occurs, for example, according to the Tofts pharmacokinetic model and by means of some mathematical models described below.

In particular, the Tofts pharmacokinetic model allows the determination of specific microvascular parameters of the tumour, such as capillary permeability, blood flow and blood volume; these parameters are calculated by interpolating in a known manner each contrast uptake curve relative to each voxel.

Instead, as regards the above-mentioned mathematical models, it is possible to use, without any loss of generality, the Weibull function and the function classes deriving from the Phenomenological Universalities (PUN); in this way, it is possible to obtain further parameters from the same images, which do not have a known direct relation with the physiology of the tumoral mass.

Figure 4:
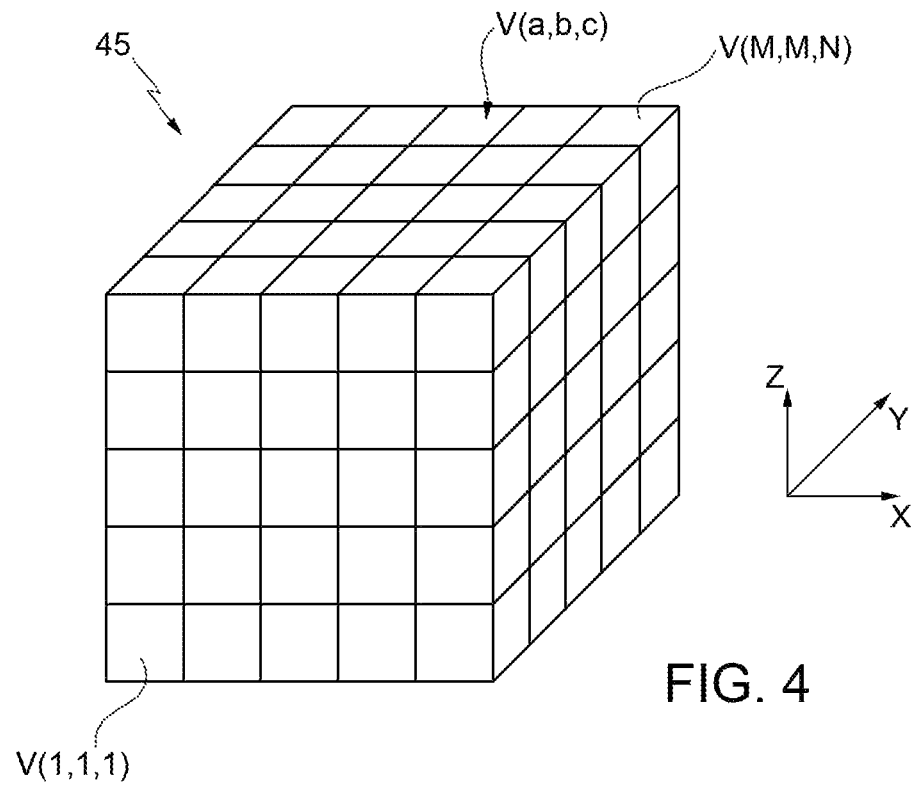
FIG. 4 shows a perspective view of a three-dimensional voxel matrix.

In light of the above, for each of the above-mentioned three acquisition techniques (T2w, DWI, DCE-MRI) a corresponding voxel three-dimensional matrix 45 (an example of which is shown in FIG. 4) is stored, for example in the processing system 4.

Furthermore, considering any matrix 45, each voxel is associated with one or more parameters (features) relative to the corresponding portion of prostatic tissue, which are stored by the processing system 4. For example, in the case of images acquired with the T2w technique, each voxel of the corresponding matrix 45 is associated with a corresponding MRI signal intensity value. Analogously, in the case of images acquired with the DWI technique, each voxel of the corresponding matrix is associated with a corresponding MRI signal intensity value. In addition, in the case of the DCE-MRI acquisition technique, each voxel is associated with the values of the above-mentioned one or more semi-quantitative and quantitative parameters obtained from the corresponding contrast uptake curve.

For the sake of brevity, the value/values of a voxel are referred to below to indicate, considering a given acquisition technique, the value/values of the corresponding parameter/s associated with the voxel in question.

In greater detail, considering any one of the three acquisition techniques, for simplicity of description it is assumed that the corresponding matrix 45 has a cubic form and is formed of voxels also having cubic form. In this regard, without any loss of generality, it is assumed that the matrix 45, and therefore also the form and arrangement of the voxels, does not depend on the acquisition technique; in fact, even if the three acquisition techniques involved, for example, voxels of different dimensions, it would be possible to achieve the described scenario by means of known processing techniques (for example, interpolation). The voxels are indicated overall by the notation V(a, b, c), in which "a", "b" and "c" are indexes which represent the spatial position of each voxel with respect to the Cartesian reference system XYZ. In greater detail, "a" is the index representative of the spatial position along a second axis X of the Cartesian reference system XYZ; "b" is the index representative of the spatial position along a third axis Y of the Cartesian reference system XYZ and "c" is the index representative of the spatial position along the first axis Z. In other words, the index c indicates the axial slice $F_i$ to which the single voxel V(a, b, c) belongs.

In practice, the voxels V(a, b, c=i=constant) define the i-th image. Furthermore, for the sake of simplicity, the voxels V(a, b, c) are represented so that voxels of successive images are arranged in contact with one another, although in reality voxels of successive images may refer to portions of prostate not necessarily adjacent to one another. In any case, below, the vertically aligned voxels of pairs of successive images are called adjacent, even when the corresponding portions of prostate are not adjacent.

Again, without any loss of generality, it is assumed that the index c is an integer variable between 1 and N, and that each of the indexes a and b is an integer variable between 1 and M (purely by way of example, in FIG. 4, M=N).

Again, with reference to FIGS. 2A-2C, the processing system 4 performs an alignment operation (block 20) of the images acquired, independently of the MRI acquisition technique used to obtain said images. Following the alignment, the images acquired by means of the above-mentioned three acquisition techniques refer to a same portion of prostate; in other words, voxels that have the same position in the three matrixes 45 acquired by means of the above-mentioned three MRI acquisition techniques refer to a same sub-portion of prostate. Equivalently, referring to a scan to indicate the group of the corresponding N images taken with a corresponding acquisition technique, the scans performed based on the above-mentioned image acquisition techniques refer to the same voxels. For this reason, below we will refer generically to a voxel to indicate the corresponding sub-portion of prostate, unless specified otherwise.

In the light of the above, it follows that each voxel is associated with a corresponding group of parameter values, referred to below as initial parameters. The parameter values include: at least one value equal to the value of said voxel in the image acquired with the T2w acquisition technique; at least one value equal to the value of the parameter ADC of said voxel; and one or more values equal to the one or more values of the semi-quantitative and quantitative parameters obtained from the corresponding contrast uptake curve.

Subsequently, the processing system 4 performs (block 30) an automatic segmentation step of the prostate 15. This automatic segmentation allows discarding of the areas external to the prostate 15 which may have been scanned previously. Below, for the sake of simplicity, it is assumed that the segmentation does not modify the images previously acquired. In a per se known manner, further operations may be performed that allow reduction of the dimensions of the images acquired; however, for the sake of simplicity it is assumed that also such possible further operations do not modify the images acquired.

Below, the processing system 4 calculates (block 40), for each voxel, at least one additional parameter, referred to below as the structural parameter (texture).

Figure 5:
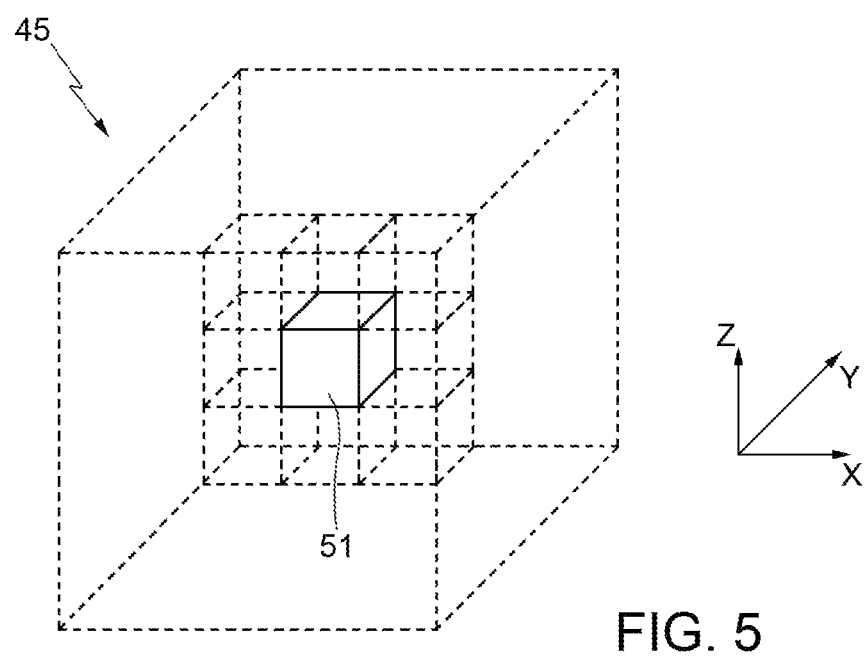
FIG. 5 shows a detail of the matrix shown in FIG. 4, with transparent parts.

In detail, referring to a generic voxel V(a, b, c) shown in FIG. 5 and indicated by the reference number 51, the corresponding structural parameter is calculated as follows.

In greater detail, the processing system 4 selects one of the above-mentioned initial parameters. Subsequently, the processing system 4 calculates the value of the structural parameter relative to the voxel 51, based on:
  the value of the selected initial parameter relative to the voxel 51; and
  the values of the selected initial parameter relative to one or more of the voxels adjacent to the voxel 51 (shown transparently in FIG. 5).

For example, indicating by AP(a,b,c) the value of the structural parameter of the voxel 51 and indicating by P(a,b,c) the value of the selected initial parameter relative to the voxel 51, the following relation applies:

$$AP(a,b,c)=P(a,b,c)+f[P(a\pm l,b\pm m,c+o)] \qquad (1)$$

where f indicates a generic dependence, while l, m and o are binary variables such that the binary string "lmo" assumes at least one sub-group of the seven values 001, 010, 011, 100, 101, 110 and 111. Variations are nevertheless possible in which one or more of l, m, o can assume values higher than one and/or variations in which one or more of three symbols "±" indicated in the above formula are substituted by the sign "+" or "−". Variations are furthermore possible in which one or more of the structural parameters each depend on the values of the corresponding initial parameter relative to voxels which, in addition to being near to the voxel 51, extend on a same plane; in this case, the following relation, for example, applies $$AP(a,b,c)=P(a,b,c)+f[P(a+l,b\pm m,c)].$$

In practice, unlike the initial parameters, which are indicative of point quantities (in the sense that they depend on physical quantities relative to the single voxel), the one or more additional parameters are each indicative of the spatial distribution of the corresponding initial parameter, in a neighbourhood of the voxel considered. In general, the definition of said neighbourhood may vary with respect to what is described; even more generally, the definition of neighbourhood may vary between the different structural parameters.

Subsequently, the processing system 4 stores (block 50), for each voxel, a plurality of corresponding values, relative both to the initial parameters and to the one or more structural parameters. Therefore, each voxel V(a, b, c) is associated with a corresponding plurality of extracted parameters, understood as including both the initial parameters and the structural parameters. For example, in the case described here, the total number of extracted parameters is equal to J.

In practice, following the operations in block 50, for each voxel, a number equal to J of corresponding parameter values are stored, which refer to the prostate 15 of any one sample patient.

Subsequently, the processing system 4 performs a selection step (block 60) of a sub-group of the J parameters extracted, which are referred to below as significant parameters.

Figure 6:
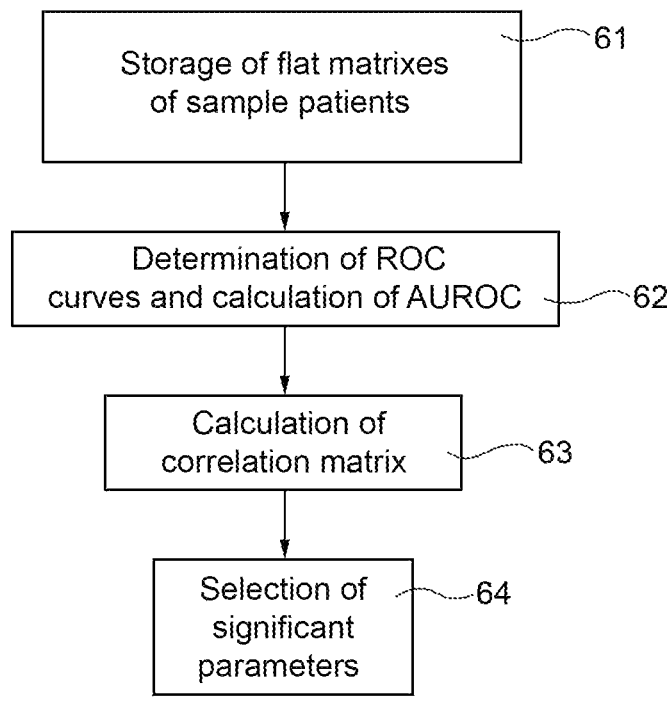

In detail, selection of the significant parameters is performed as shown in FIG. 6.

Considering each sample patient and the outcome of the corresponding surgery, an operator associates with each voxel of the sample patient a binary indication relative to the presence/absence of tumour in said voxel, based on the pathological indications provided by the prostate samples. Said association is also stored in the processing system 4.

Figure 7:
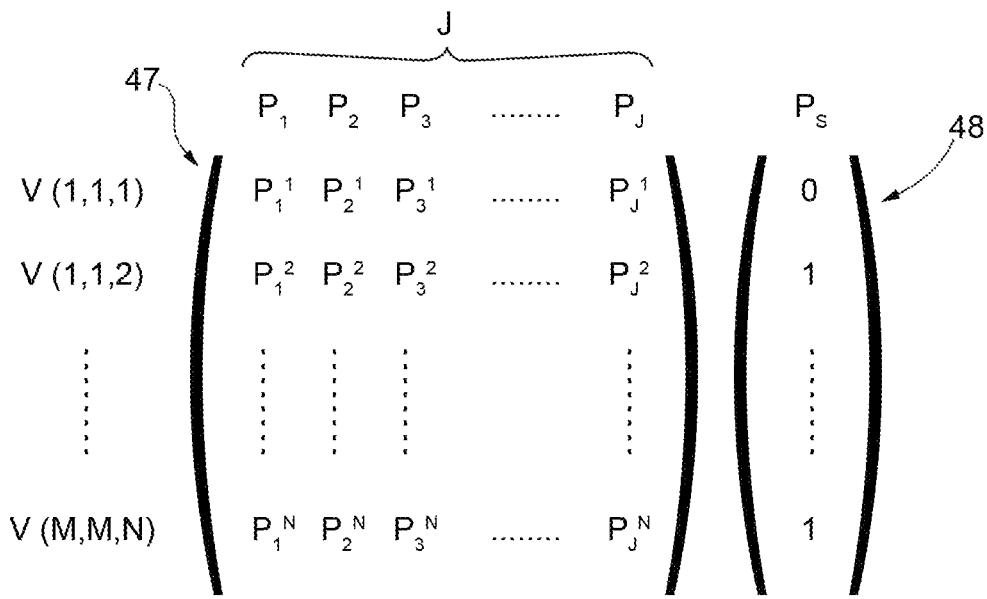
FIGS. 7 and 11 show matrixes of parameter values acquired by the present detection system.

In practice, the processing system 4 stores (block 61, FIG. 6), for each sample patient, a flat matrix 47 and a vector 48, shown for example in FIG. 7.

In detail, the flat matrix 47 has N×M² lines which correspond to the voxels. Furthermore, the flat matrix 47 shows, for each voxel, the corresponding values of the extracted parameters. On the other hand, the vector 48 contains, for each voxel, the corresponding binary indication (indicated as $P_s$, while the extracted parameters are indicated by $P_p$, where p is an integer index ranging from 1 to J). In the example of FIG. 7, the flat matrix 47 and the vector 48 refer, for example, to a first sample patient.

Subsequently, the processing system 4 determines (block 62, FIG. 6), for each of the extracted parameters, a corresponding ROC (Receiver Operating Characteristic) curve, which indicates the ability of each parameter to distinguish between malignant tissue and healthy tissue, and calculates the area below (also defined as AUROC, Area Under ROC).

In particular, to obtain the ROC curve of any one of the extracted parameters, the processing system 4 selects the columns (in a number equal to Q) of the flat matrixes 47 relative to the sample patients corresponding to the extracted parameter considered, obtaining a macrocolumn 300 (shown in FIG. 8 and referring, for example and without any loss of generality, to the first extracted parameter Pi), given by the succession of the columns selected. Furthermore, said macrocolumn 300 is associated with a macrovector 310 (shown in FIG. 8) given by the succession of the vectors 48 relative to the sample patients.

Subsequently, the processing system 4 arranges the values of the macrocolumn 300 in increasing order; this operation entails a corresponding reordering of the binary indications of the macrovector 310, so as to maintain the original voxel-binary indication associations.

Subsequently, the processing system 4 repeats the following operations, for each of the values of the extracted parameter considered (below indicated by W):

sets a threshold (cut-off) equal to said value W of the extracted parameter considered; and calculates a sensitivity parameter S(W) and a specificity parameter Sp(W).

In particular, the sensitivity is defined in the equation (2) as:

$$S(W) = \frac{VP}{VP+FN} \quad (2)$$

wherein VP is the number of true positives and FN is the number of false negatives of the Q×N×M² values of the extracted parameter considered, the true positive and the false negatives being determined as follows:

the true positives are given by the values above the threshold and associated with binary indications indicative of the presence of tumour; and the false negatives are given by the values below the threshold and associated with binary indications indicative of the presence of tumour.

On the other hand, the specificity is defined in the equation (3) as:

$$Sp(W) = \frac{VN}{VN+FP} \quad (3)$$

wherein VN is the number of true negatives and FP is the number of false positives of the Q×N×M² values of the extracted parameter considered, which are determined as follows:

the true negatives are given by the values below the threshold and associated with binary indications indicative of the absence of tumour; and the false positives are given by the values above the threshold and associated with binary indications indicative of the absence of tumour.

Figure 9:
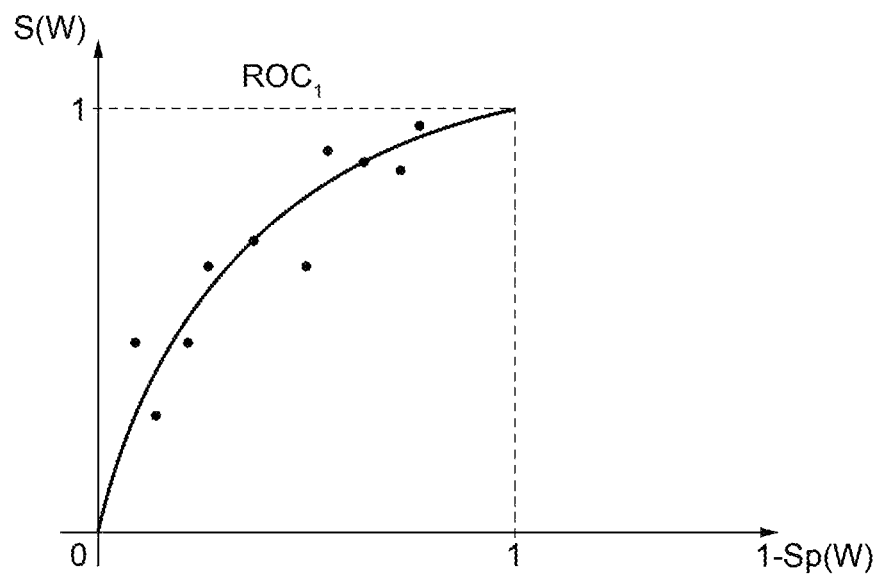
FIG. 9 shows an example of curve trend calculated by the present detection system, in a Cartesian diagram.

At the end of the repetitions, the processing system 4 is therefore able to store, for each threshold value previously set, a corresponding point of the ROC curve referring to the corresponding extracted parameter considered; in particular, as shown in FIG. 9, said point has an X axis equal to the difference between one and the specificity 1-Sp(W) and a Y axis equal to the sensitivity S(W). Subsequently, the processing system 4 interpolates the points and obtains the corresponding ROC curve; for example, as mentioned previously, FIG. 9 shows an $ROC_1$ curve that refers to the first extracted parameter Pi.

At the end of the operations in block 62 of FIG. 6, the processing system 4 has as many ROC curves as columns of each flat matrix 47; in particular, in the case considered, the processing system 4 generates J ROC curves.

Subsequently, although not shown, the processing system 4 calculates the area below each ROC curve, therefore associating a numeric value with each extracted parameter $P_p$.

Figure 10:
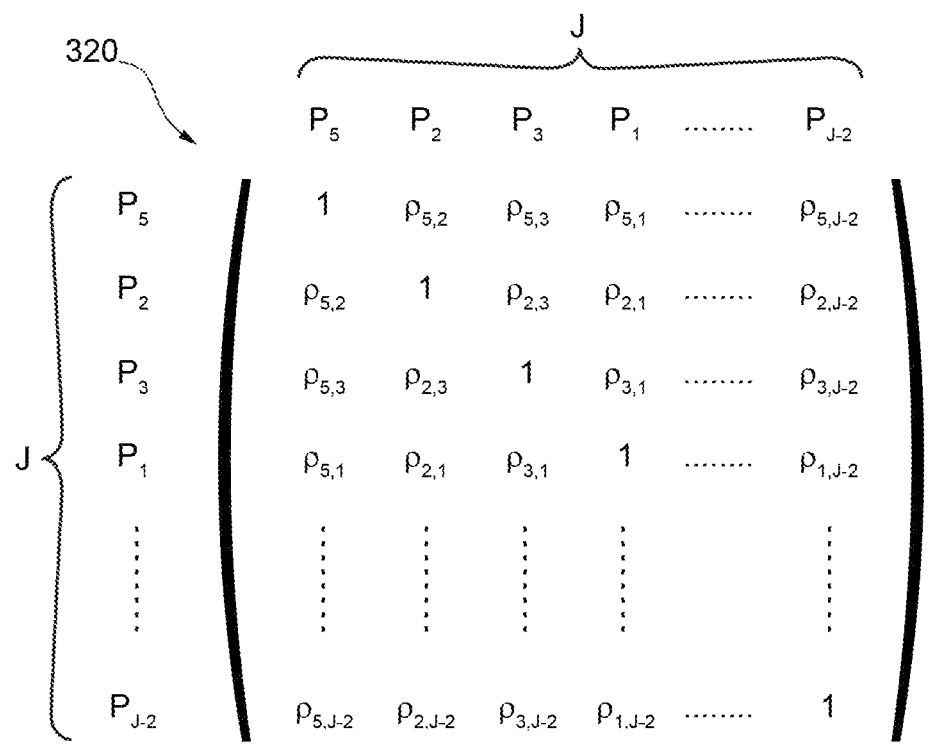
FIGS. 10, 18 and 24 show examples of correlation matrixes determined by the present detection system.

The processing system 4 determines (block 63), therefore, a correlation matrix, by means of the linear correlation method in pairs. An example of correlation matrix is shown in FIG. 10 and is indicated by the reference number 320; in particular, this correlation matrix 320 is constructed so that the extracted parameters are organised, on the lines and on the columns, in decreasing order (from top to bottom, and therefore also from left to right) based on the area below the respective ROC curve. In said regard, the greater the area below the ROC curve, the greater the specificity and the sensitivity associated with the corresponding parameter extracted for determining the presence/absence of a tumoral mass.

In detail, for each possible pair of extracted parameters, a corresponding correlation coefficient is defined, based on the corresponding pair of macrocolumns 300. In general, the correlation coefficient varies between −1 (in the case of inversely correlated parameters) and +1 (in the case of directly correlated parameters) and is equal to zero in the case of totally uncorrelated parameters.

In particular, the correlation matrix 320 is a symmetrical matrix J×J, on the diagonal of which the correlation of each parameter with itself (therefore, equal to 1) is shown and in the other positions the correlation coefficients of the pairs of extracted parameters are shown. In FIG. 10, each correlation parameter is indicated by the reference $\rho_{e,f}$, in which e and f are indexes referring to the extracted parameters, the calculation of the correlation of which is desired.

Subsequently, the processing system 4 selects (block 64, FIG. 6) the significant parameters, based on the correlation matrix 320 constructed in the preceding step, in which the parameters were ordered in decreasing values of the area below the ROC curve.

In particular, the processing system 4 analyses in sequence all the correlation coefficients of the over-diagonal or under-diagonal half of the correlation matrix 320. For example, assuming that the over-diagonal half of the correlation matrix 320 is analysed, it is analysed by lines, from top to bottom, and from left to right. Furthermore, when a pair of extracted parameters has a degree of correlation equal to or greater than 80% (i.e. if $\rho_{e,f} \geq 0.8$, excluding the correlation coefficients arranged on the main diagonal of the correlation matrix 320), the processing system 4 chooses the parameter of the pair whose ROC curve subtends the larger area, and discards the other; this means that, proceeding in the analysis of the correlation coefficients, the correlation coefficients that involve the discarded parameter will not be considered. The analysis therefore continues without considering the parameters that are gradually discarded, as far as the last correlation coefficient of the over-diagonal half. In practice, whenever a pair of extracted parameters with correlation coefficient equal to or greater than 80% meet, only the parameter most representative of the presence/absence of prostate tumoral masses is chosen (maintained), therefore the processing system 4 continues to consider it as a possible significant parameter, unlike the discarded parameter.

Below it is assumed, for example, that the operations in block result in the selection of a number S of significant parameters (with S<J); this selection is stored by the processing system 4.

Figure 11:
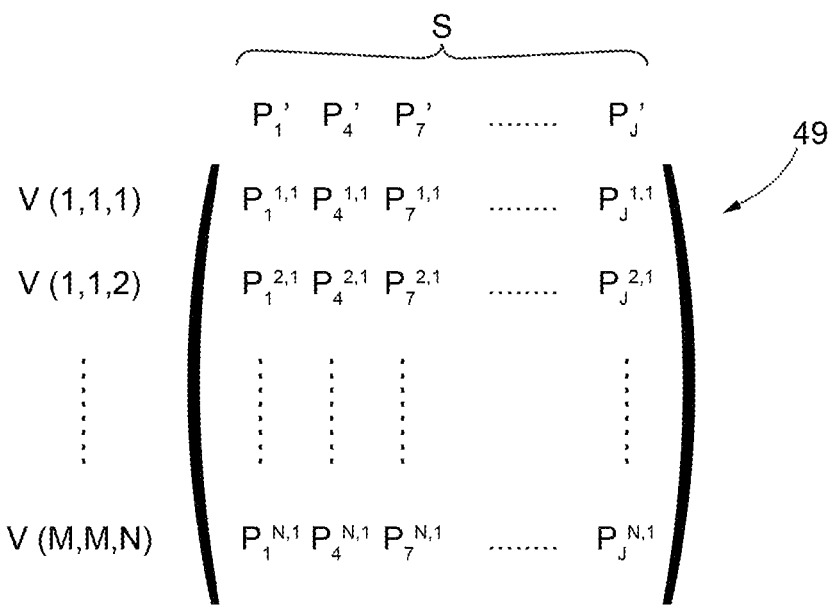

Again, with reference to FIGS. 2A-2C, the processing system 4 selects (block 65 of FIG. 2A), within the flat matrix 47 referring to each sample patient, only the columns relative to the significant parameters, thus reducing the number of columns of the flat matrix 47 relative to each sample patient. In this way, a reduced matrix 49 is obtained, an example of which is shown in FIG. 11 (in which the significant parameters are indicated by the same signs as the corresponding extracted parameters, with the addition of a superscript). In detail, the reduced matrix 49 shown in FIG. 11 refers, for example, to the first sample patient and has N×M² lines, representing the voxels, and S columns, representing the significant parameters.

Again, with reference to FIG. 2A, the processing system 4 determines (block 70) a first classifier, based on the values of the significant parameters $P_p'$ contained in the reduced matrixes 49 of the sample patients and the corresponding binary indications indicative of the presence of tumour.

In particular, the processing system 4 generates and stores a classifier of known type (for example, SVM, Support Vector Machine classifier, as described for example in "Machine learning in medical imaging", IEEE Signal Process Magazine, 2010 July, 27(4): 25-38, di M. N. Wernick et al.), i.e. a mathematical model adapted to receive as input data the values of the significant parameters $P_p'$ of any one voxel of any one patient and generate at output a corresponding value indicative of the probability that said voxel represents a tumoral voxel. The group of the probability values forms a corresponding map, which associates, with each voxel V(a, b, c), a corresponding probability of representing a tumoral voxel; this map is referred to below as three-dimensional likelihood map.

Again with reference to FIG. 2B, and again with reference to each sample patient, the processing system 4 carries out a selection (block 80) of the voxels of the corresponding three-dimensional likelihood map which have probability values greater than or equal to, for example, 60%.

In particular, referring to the planar matrix of voxels to indicate, given any axial slice $F_i$, the corresponding voxels V(a, b, c=i), the processing system 4 stores, for each planar matrix of voxels, the areas formed by voxels which respond to the selection criterion described (probability value greater than or equal to, for example, 60%) and are furthermore adjacent to one another; therefore, the above-mentioned areas represent corresponding isolated selected voxels or corresponding aggregates of selected voxels. Below this areas will be referred to as two-dimensional regions of voxels.

Figure 12:
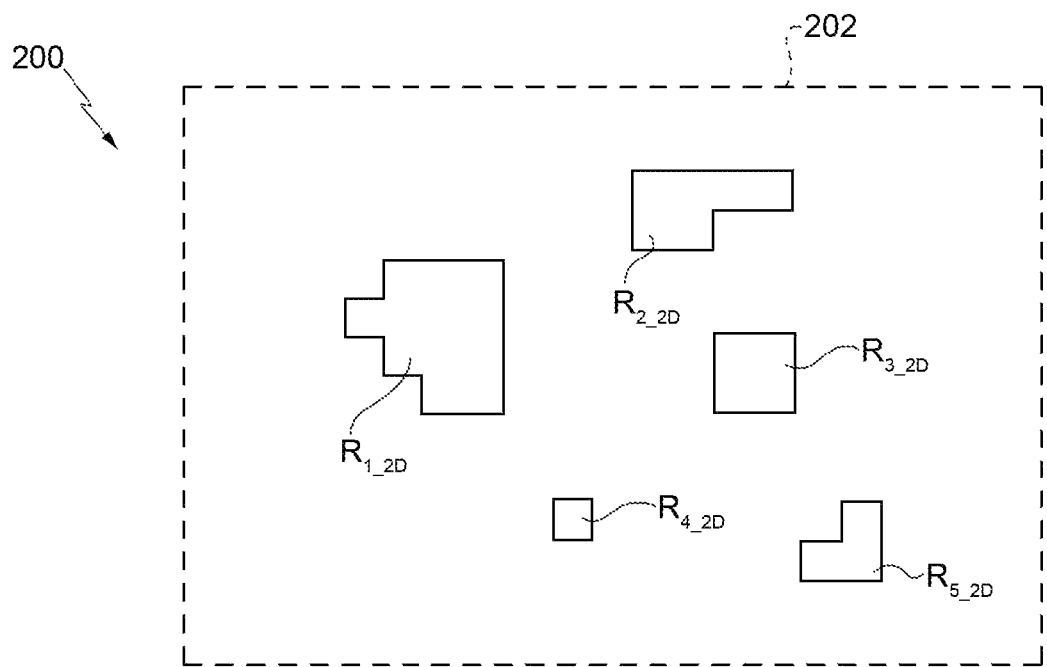
FIG. 12 schematically shows a section of a probability map determined by the present detection system.

For example, FIG. 12 refers to the first sample patient and shows a section 200 of the corresponding three-dimensional likelihood map, in which a plurality of two-dimensional regions of voxels $R_{1\_2D}$-$R_{5\_2D}$ and a portion of remaining map 202 are present. In practice, the portion of remaining map 202 is the portion of the section 200 complementary to the plurality of two-dimensional regions of voxels $R_{1\_2D}$-$R_{5\_2D}$; the portion of remaining map 202 therefore represents the group of voxels of the section 200 having probability of presenting a tumoral mass (for example) lower than 60%.

Subsequently, the processing system 4 determines (block 90; FIG. 2B) the dimension of each of the two-dimensional regions of voxels, which is equal to the number of voxels constituting each of the above-mentioned two-dimensional regions of voxels.

Subsequently, the processing system 4 compares (block 100; FIG. 2B) the dimension of each two-dimensional region of voxels with a predefined threshold value, for example equal to 100 mm². In particular, if the dimensions of a two-dimensional region of voxels are lower than the threshold value, the processing system 4 discards the region (block 110; FIG. 2B). Below, we refer to the two-dimensional regions selected to indicate the two-dimensional regions of voxels having dimensions greater than the threshold value.

In addition, the processing system 4 carries out a further selection step (optional), in which, in each two-dimensional region selected, any "noisy" voxels are removed.

In detail, analysing any one of the representations obtained by means of one of the three acquisition techniques previously discussed and considering the initial parameters that can be obtained for each voxel of a given representation, a voxel is defined "noisy" if considered as representative of a false positive. For example, for images acquired by means of DCE-MRI acquisition technique, the processing system 4 analyses the contrast uptake curve referring to each voxel forming the selected two-dimensional region under investigation. It is observed that a voxel is indicative of the actual presence of a prostate tumour if, after approximately 60 seconds from injection of the contrast medium (for example, at the time instant $t_4'$ or at the time instant $t_5'$, in the case of temporal resolution equal to 13 seconds), the contrast uptake curve presents a rapid ascent; consequently, it is possible to discard the voxels having less marked contrast uptake curves without the rapid ascent described, since these voxels are not effectively representative of prostate tissues affected by tumour. Below, for the sake of simplicity, it is assumed that the step of removal of the noisy voxels is not carried out.

Subsequently, the processing system 4 carries out a step of determination (block 120; FIG. 2B) of three-dimensional regions of voxels.

In detail, a three-dimensional region of voxels is defined when at least two selected two-dimensional regions, belonging to two planar matrixes of adjacent voxels, are connected, or are at least partially overlapped along the first axis Z of the Cartesian reference system XYZ.

Figure 13:
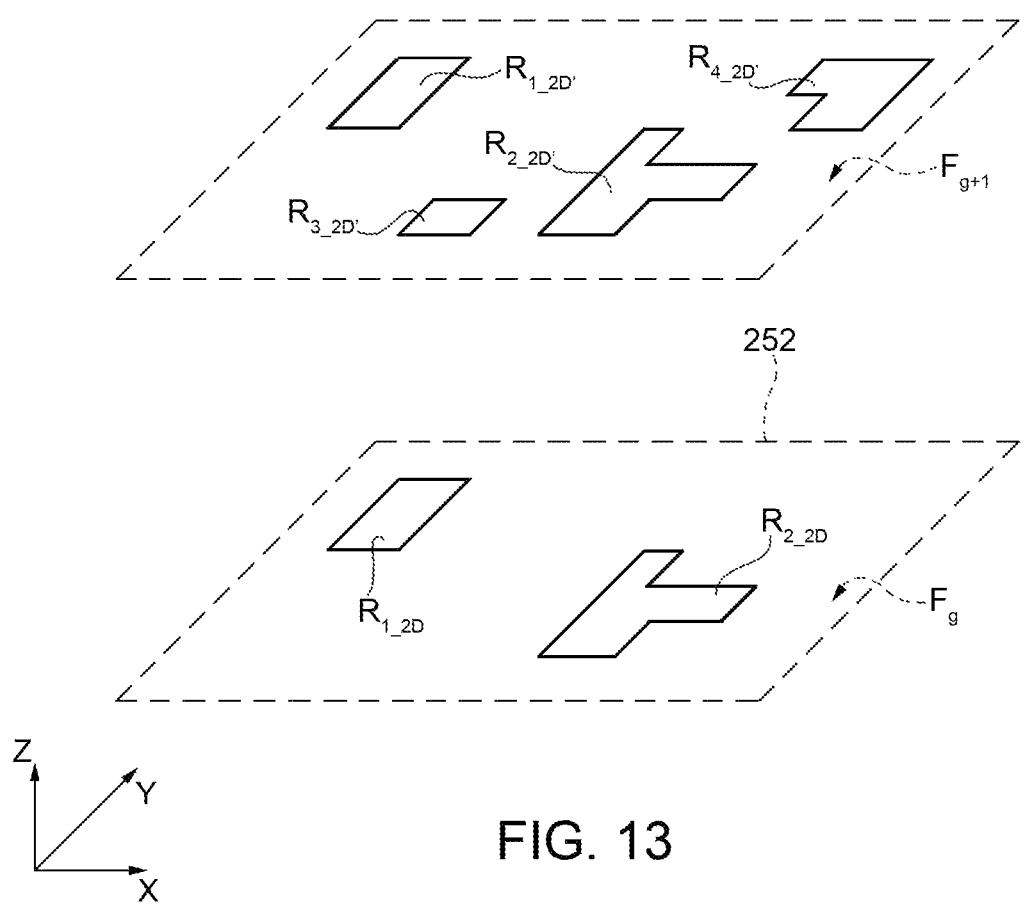
FIG. 13 schematically shows a perspective view of two sections of a probability map determined by the present detection system.

An example of evaluation of the connection of selected two-dimensional regions is shown in FIG. 13. In detail, FIG. 13 shows a first and a second planar matrix of voxels (indicated by the references $F_g$, $F_{g+1}$ of the corresponding axial slices, in which g is an index between 1 and N−1), each including its own plurality of selected two-dimensional regions. In particular, the first planar matrix of voxels $F_g$ comprises a first and a second selected two-dimensional region $R_{1\_2D}$, $R_{2\_2D}$; analogously, the second planar matrix of voxels $F_{g+1}$ comprises a third, a fourth, a fifth and a sixth selected two-dimensional region $R_{1\_2D}'$, $R_{2\_2D}'$, $R_{3\_2D}'$ and $R_{4\_2D}'$.

In detail, the first selected two-dimensional region $R_{1\_2D}$ is vertically aligned with the third selected two-dimensional region $R_{1\_2D}'$; analogously, the second selected two-dimensional region $R_{2\_2D}$ is vertically aligned with the fourth selected two-dimensional region $R_{2\_2D}'$.

On the other hand, the fifth and the sixth selected two-dimensional regions $R_{3\_2D}'$, $R_{4\_2D}'$ overlap the remaining map portion 252 of the planar matrix of voxels $F_g$.

In other words, the first and the second selected two-dimensional regions $R_{1\_2D}'$, $R_{2\_2D}'$ are respectively connected to the third and the fourth selected two-dimensional regions $R_{1\_2D}'$, $R_{2\_2D}'$. Furthermore, in the example proposed and for the sake of simplicity of representation, the first and the second selected two-dimensional regions of voxels $R_{12D}$, $R_{2\_2D}$ have the same forms as the third and the fourth selected two-dimensional regions of voxels $R_{1\_2D}'$, $R_{2\_2D}'$.

Figure 14:
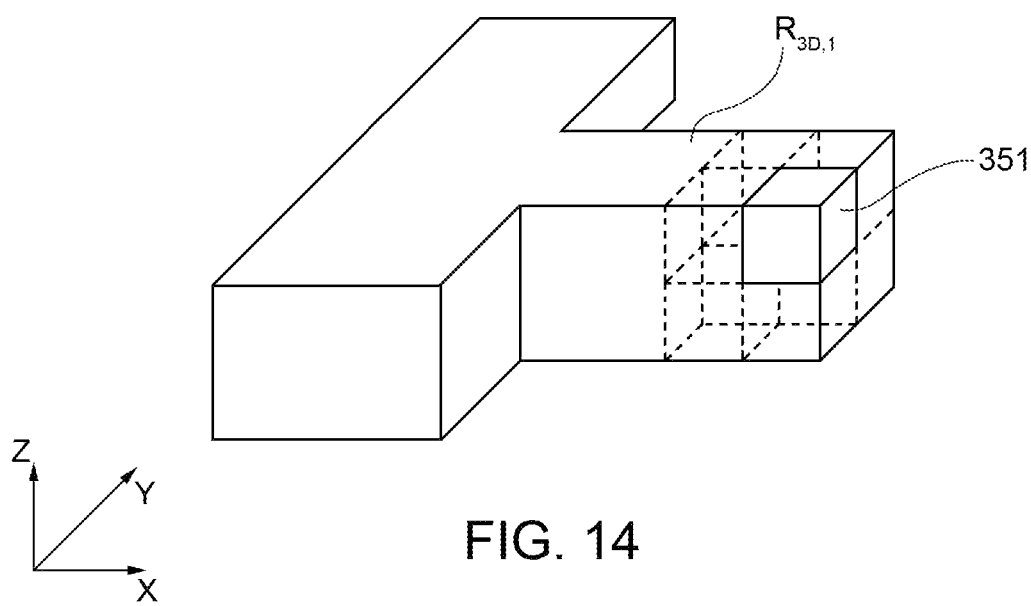
FIGS. 14 and 20 schematically show perspective views of three-dimensional regions of voxels.

At the end of the operations in block 120 (FIG. 2B), the processing system 4 stores the three-dimensional regions of voxels previously determined. An example of three-dimensional region of voxels referring, for example, to the first sample patient, is shown in FIG. 14, where it is indicated by $R_{3D,1}$; by way of example, FIG. 14 shows a voxel 351 belonging to the three-dimensional region of voxels $R_{3D,1}$.

Again with reference to FIG. 2B, the processing system 4 calculates, for each three-dimensional region of voxels, at least one regional parameter (block 130).

In detail, the processing system 4 selects one of the initial parameters. Subsequently, for each three-dimensional region of voxels, the processing system 4 calculates the corresponding value of the regional parameter based on the values of the initial selected parameter of the voxels that form the three-dimensional region of voxels. For example, possible regional parameters can be given by parameters indicative of the contrast and/or homogeneity of the three-dimensional regions of voxels, calculated on the basis of the values of corresponding initial parameters. For example, for each three-dimensional region of voxels, the processing system 4 may calculate values indicative, respectively: of the homogeneity of the intensity of the MRI signal acquired with the T2w acquisition technique; of the contrast of the intensity of the MRI signal acquired with the T2w acquisition technique; of the homogeneity of the ADC parameter acquired with the DWI acquisition technique; of the contrast of the ADC parameter acquired with the DWI acquisition technique; of the homogeneity of the intensity of the MRI signal acquired with the DCE acquisition technique in any one of the above-mentioned instants $t_0'$-$t'_{k-1}$; and of the contrast of the intensity of the MRI signal acquired with the acquisition technique DCE in any one of the above-mentioned instants t0'−t'k−1. Other values may also be calculated such as, for example, entropy values, as described in R. M. Haralick, K. Shanmugam, and I. Dinstein, "Textural Features of Image Classification", IEEE Transactions on Systems, Man and Cybernetics, vol. SMC-3, no. 6, November 1973, or energy values, again based on the signals acquired with one or more of the above-mentioned acquisition techniques. Further examples of possible regional parameters are represented by statistical parameters (for example, the mean, median and percentiles) of the intensity of the MRI signal acquired according to one or more of the three acquisition techniques.

Subsequently, the processing system 4 stores, for each sample patient, the regional parameters determined in the preceding step (block 140; FIG. 2B). In detail, for each three-dimensional region of voxels, a number equal to L of values of corresponding regional parameters is stored.

Subsequently, the processing system 4 carries out a selection step (block 150; FIG. 2B) of a sub-group of the L regional parameters, referred to below as significant regional parameters.

In detail, selection of the significant regional parameters is carried out as described below.

An operator associates with each three-dimensional region of voxels of each sample patient a binary indication relative to the degree of aggressiveness of the tumour in said three-dimensional region of voxels.

In order to have said association, each three-dimensional region of voxels considered undergoes a preliminary evaluation by a pathologist.

In detail, each three-dimensional region of voxels is associated by the pathologist with two numerical references according to the known Gleason score system. In particular, each three-dimensional region of voxels is assigned:

a first integer index, variable from 1 to 5, relative to the aggressiveness of the dominant cell morphology (i.e. commonest) in the three-dimensional region of voxels considered, indicated below by the notation in_1;

a second integer index, also variable from 1 to 5, relative to the aggressiveness of the second commonest cell morphology in the three-dimensional region of voxels (on the condition that it has an extension at least equal to 5% of the three-dimensional region of voxels, otherwise the second index is set equal to the first index), indicated below by the notation in_2.

For each three-dimensional region of voxels, the Gleason score $I_{3D}$ is obtained, defined as a combination of in_1 and in_2. For example, for the three-dimensional region of voxels $R_{3D,1}$ the Gleason score $I_{3D}$ can be equal to 4+3.

The operator then associates '0' with the three-dimensional regions of voxels having Gleason score $I_{3D}$ lower than or equal to (for example) 3+3 and associates '1' with the three-dimensional regions of voxels having Gleason score $I_{3D}$ higher than 3+3.

Figure 15:
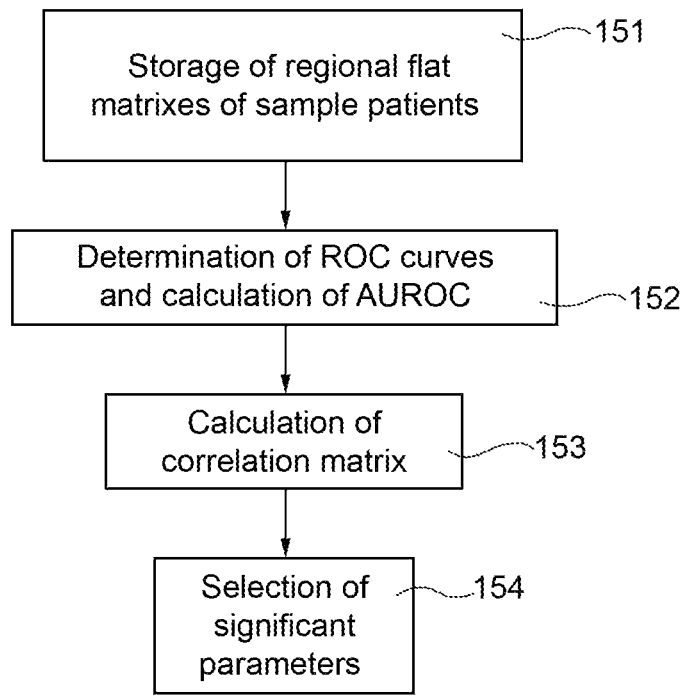

Subsequently, as shown in FIG. 15, the processing system 4 stores (block 151), for each sample patient, a regional flat matrix 247 and a regional vector 248, shown for example in FIG. 16, relative to the first sample patient.

Figure 16:
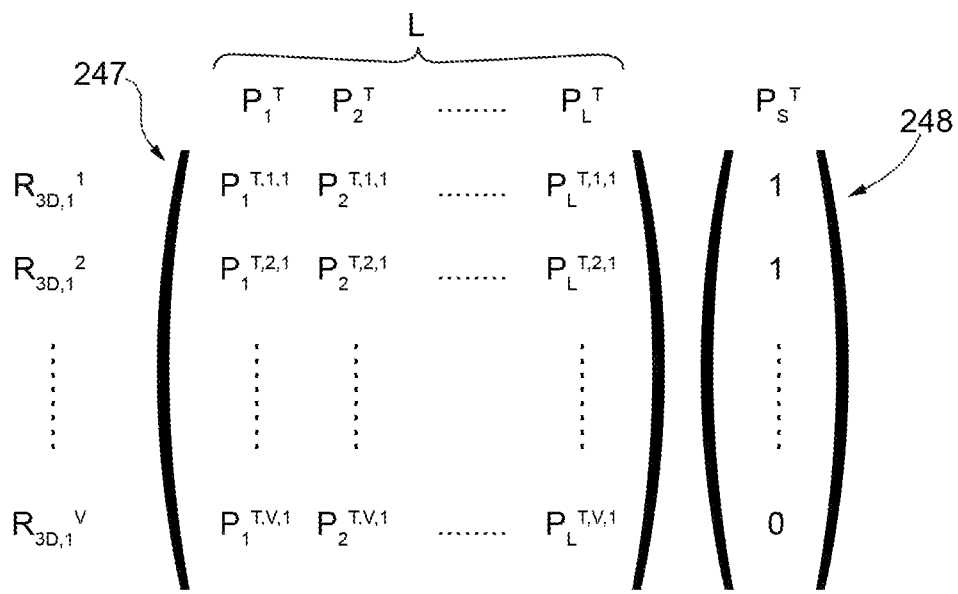
FIGS. 16 and 19 show matrixes of regional parameter values determined by the present detection system.

The regional flat matrix 247 has as many lines as the number of three-dimensional regions of voxels identified for the corresponding sample patient; in the example shown in FIG. 16, the first sample patient has V three-dimensional regions of voxels.

The regional flat matrix 247 shows, for each three-dimensional region of voxels, the corresponding values of the regional parameters; therefore, the regional flat matrix 247 has dimensions equal to V×L. On the other hand, the regional vector 248 contains, for each three-dimensional region of voxels, the corresponding binary indication relative to the aggressiveness (indicated as $P_s^T$, while the parameters are indicated by $P_r^T$, where r is an integer index ranging from 1 to L).

Figure 17:
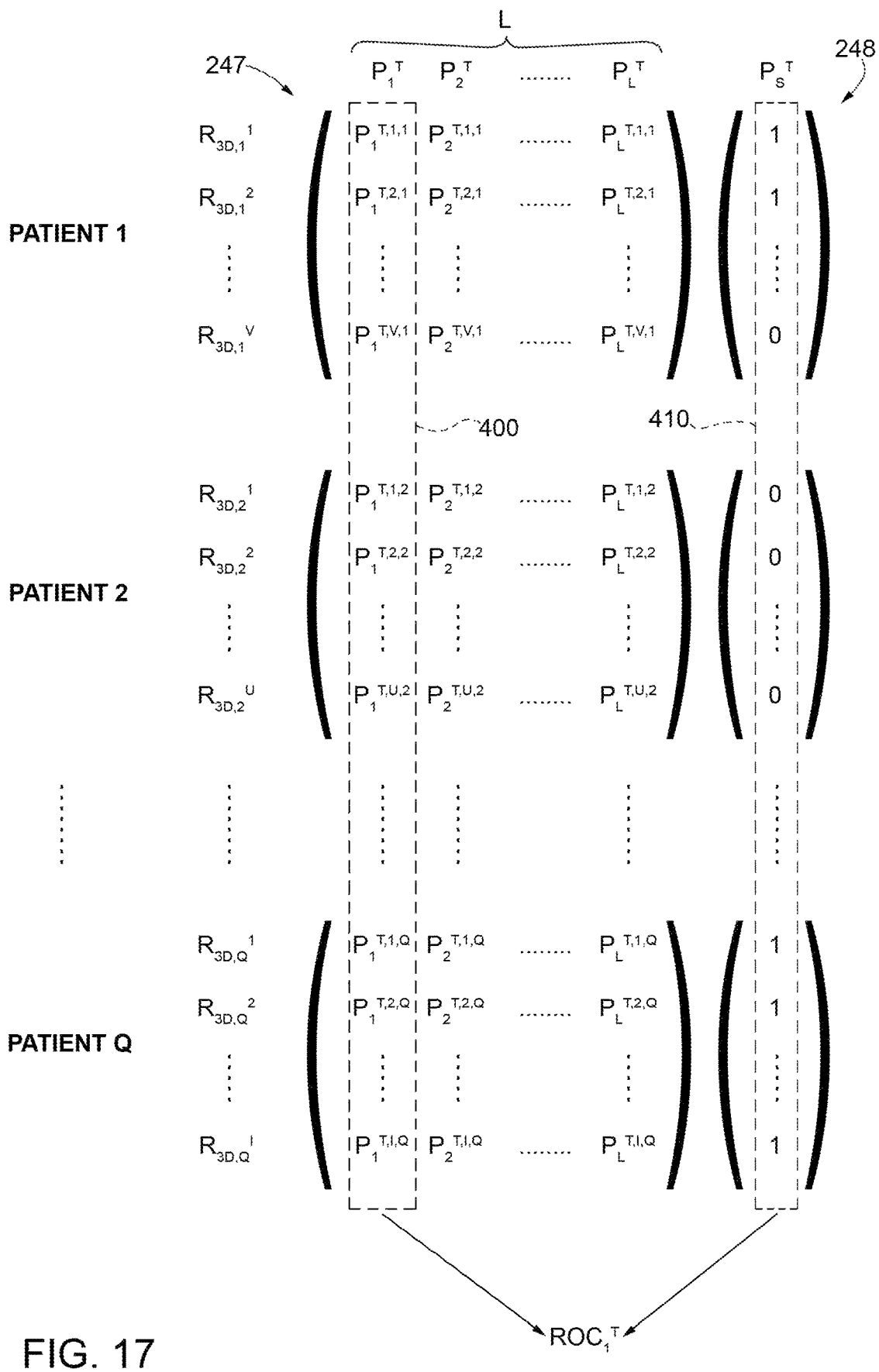
FIG. 17 shows matrixes of regional parameter values used during a further curve trend determination step performed by the present detection system.

Subsequently, the processing system 4 determines (block 152), for each of the regional parameters, a corresponding $ROC^T$ regional curve and the relative area, in the same way as discussed with reference to block 62, with the exception of the fact that the calculation is performed based on a regional macrocolumn 400 (FIG. 17) given by the columns (in a number equal to Q) of the regional flat matrixes 247 which correspond to the regional parameter considered, and based on a regional macrovector 410 given by the succession of regional vectors 248 relative to the sample patients.

Figure 18:
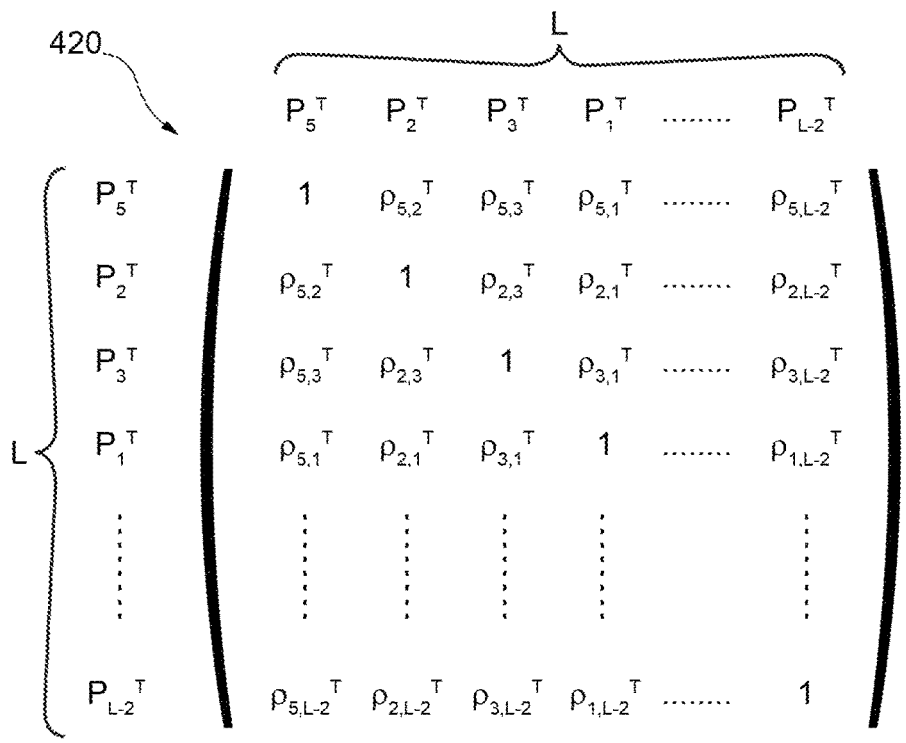

Subsequently, the processing system 4 determines (block 153) a regional correlation matrix (shown in FIG. 18, where it is indicated by 420), carrying out the same operations described with reference to block 63, with the exception of the fact that these operations are performed on the regional macrocolumns 400.

Subsequently, the processing system 4 selects (block 154) the significant regional parameters, based on the regional correlation matrix 420, performing the same operations as those described for block 64, without prejudice to the possibility of adopting a different threshold value from the one used in the operations in block 64.

Below it is assumed, for example, that the operations described so far result in choosing and storing a number H of significant regional parameters (with H<L).

Figure 19:
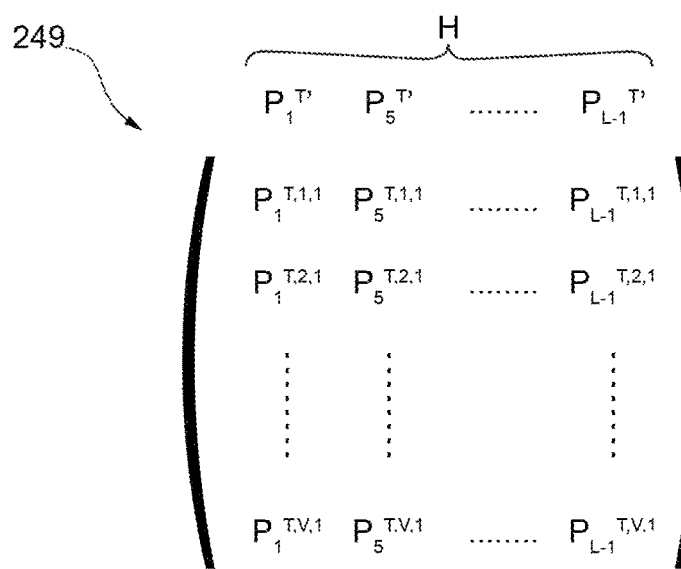

Again with reference to FIG. 2B, the processing system 4 selects (block 160), from within the regional flat matrix 247 of each sample patient, only the columns relative to the significant regional parameters. In this way, a corresponding reduced regional matrix 249 is obtained, an example of which, relative to the first sample patient, is shown in FIG. 19, in which the significant regional parameters are indicated by the addition of a superscript.

Subsequently, the processing system 4 determines (block 170 of FIG. 2B) a second classifier (for example, of Bayes type, or decision tree, SVM (as described for example in Kononenko, I., I. Bratko and M. Kukar, 1998. Application of Machine Learning to Medical Diagnosis. In: Machine Learning and Data Mining: Methods and Applications, R. S. Michalski, I. Bratko and M. Kubat (Eds.). J. Wiley, New York), based on the values of the significant regional parameters $P_r^{T'}$ contained in the reduced regional matrixes 249 of the sample patients and of the corresponding binary indications $P_s^T$. In particular, the processing system 4 generates and stores a mathematical model adapted to receive as input data the values of the significant regional parameters $P_r^{T'}$ of any one three-dimensional region of voxels of any one patient and generate at output a corresponding indication of the degree of aggressiveness of the tumoral mass present in said three-dimensional region of voxels.

Again, with reference to FIG. 2C, the processing system 4 selects (block 171) the three-dimensional regions of voxels associated with '1', which are referred to below as relevant three-dimensional regions.

Figure 20:
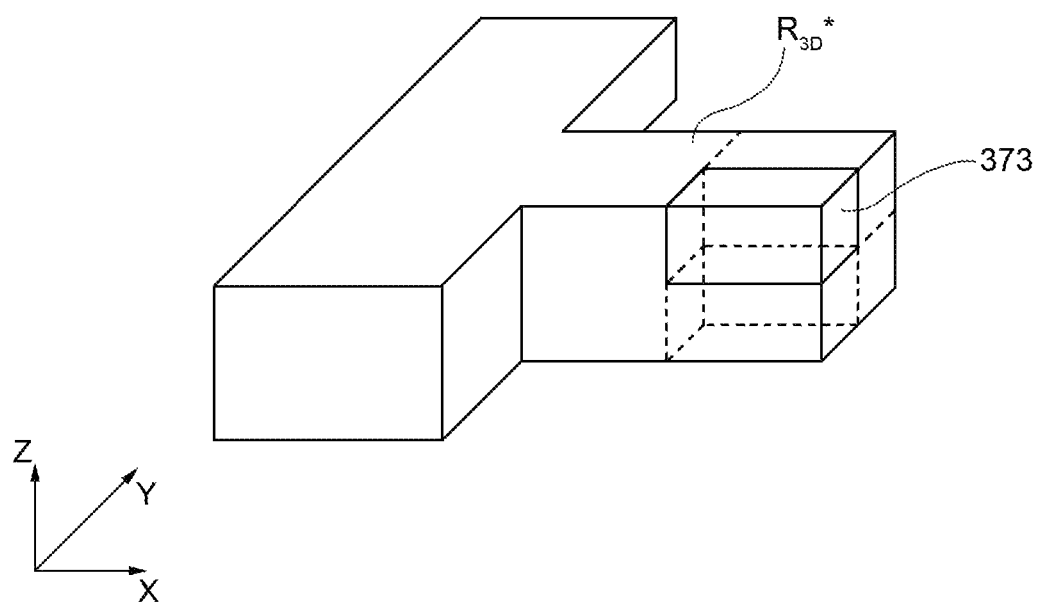

Subsequently, for each relevant three-dimensional region of each sample patient, the processing system 4 divides (block 172; FIG. 2C) the relevant three-dimensional region into a plurality of cells, as shown for example in FIG. 20, where the cells (four) are indicated by 373 and the relevant three-dimensional region is indicated by $R_{3D}^*$. In particular, the cells 373 have for example the same form (predefined), so as to form a regular lattice. The cells 373 are each formed of a corresponding group of adjacent voxels (for example, in the shape of parallelepipeds or cubes); furthermore, the cells 373 are also adjacent to one another, so as to cover, as a whole, the entire relevant three-dimensional region. In practice, each cell covers a corresponding portion of the relevant three-dimensional region to which it belongs.

Subsequently, for each cell 373, the processing system 4 calculates (block 173; FIG. 2C) a corresponding group of parameter values, which are referred to below as cell parameters. In particular, the cell parameters may be respectively equal to the above-mentioned regional parameters, apart from the fact that they are calculated on the domain of the cell, instead of on the entire three-dimensional region of voxels. The cell parameters may therefore be formed, for example, from parameters indicative of the contrast and/or the homogeneity and/or the entropy and/or the energy and/or of statistical parameters of the cells of voxels, calculated on the basis of the values of corresponding initial parameters of the voxels that form the cells. Below it is assumed that the number of cell parameters is, for example, equal to D.

Subsequently, the processing system 4 stores (block 174; FIG. 2C), for each sample patient, the cell parameters determined in the preceding step.

Subsequently, the processing system 4 carries out a new selection step (block 175; FIG. 2C) of a sub-group of the cell parameters, which will be referred to below as significant cell parameters.

In detail, the significant cell parameters are selected as described below.

An operator associates with each cell of each sample patient a binary indication relative to the degree of aggressiveness of the tumour in said cell. In order to have this association, each cell undergoes a preliminary evaluation by a pathologist, who associates a value '1' if he/she considers the cell aggressive (for example, if it has a Gleason score higher than or equal to three), or associates a value '0' if he/she considers the cell non-aggressive.

Figure 21:
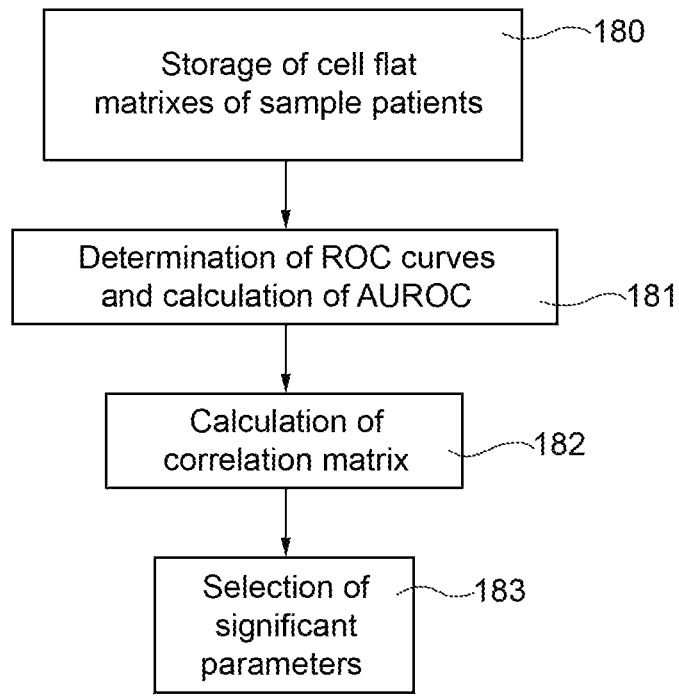

Subsequently, as shown in FIG. 21, the processing system 4 stores (block 180), for each sample patient, a flat cell matrix 347 and a cell vector 348, shown for example in FIG. 22, relative to the first sample patient.

Figure 22:
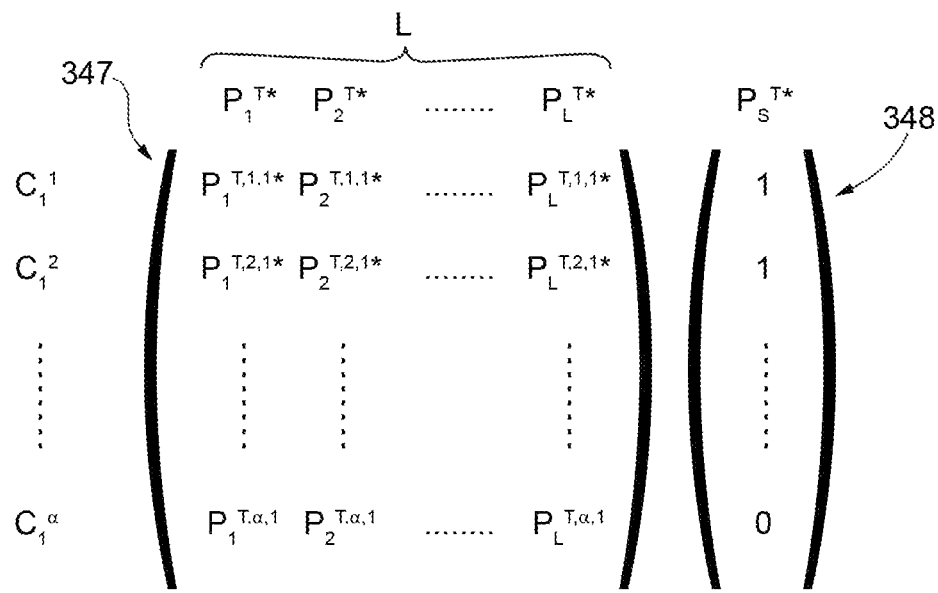
FIGS. 22 and 25 show matrixes of cell parameter values determined by the present detection system.

The flat cell matrix 347 has as many lines as the cells identified for the corresponding sample patient; in the example shown in FIG. 22, the first sample patient has overall α cells, independently of how these cells are shared between the relevant three-dimensional regions of the first sample patient.

The flat cell matrix 347 shows, for each cell, the corresponding values of the cell parameters; therefore, the flat cell matrix 347 has dimensions equal to α×D. On the other hand, the cell vector 348 contains, for each cell, the corresponding binary indication relative to the aggressiveness (indicated as $P_s^{T*}$, while the cell parameters are indicated by $P_r^{T*}$).

Figure 23:
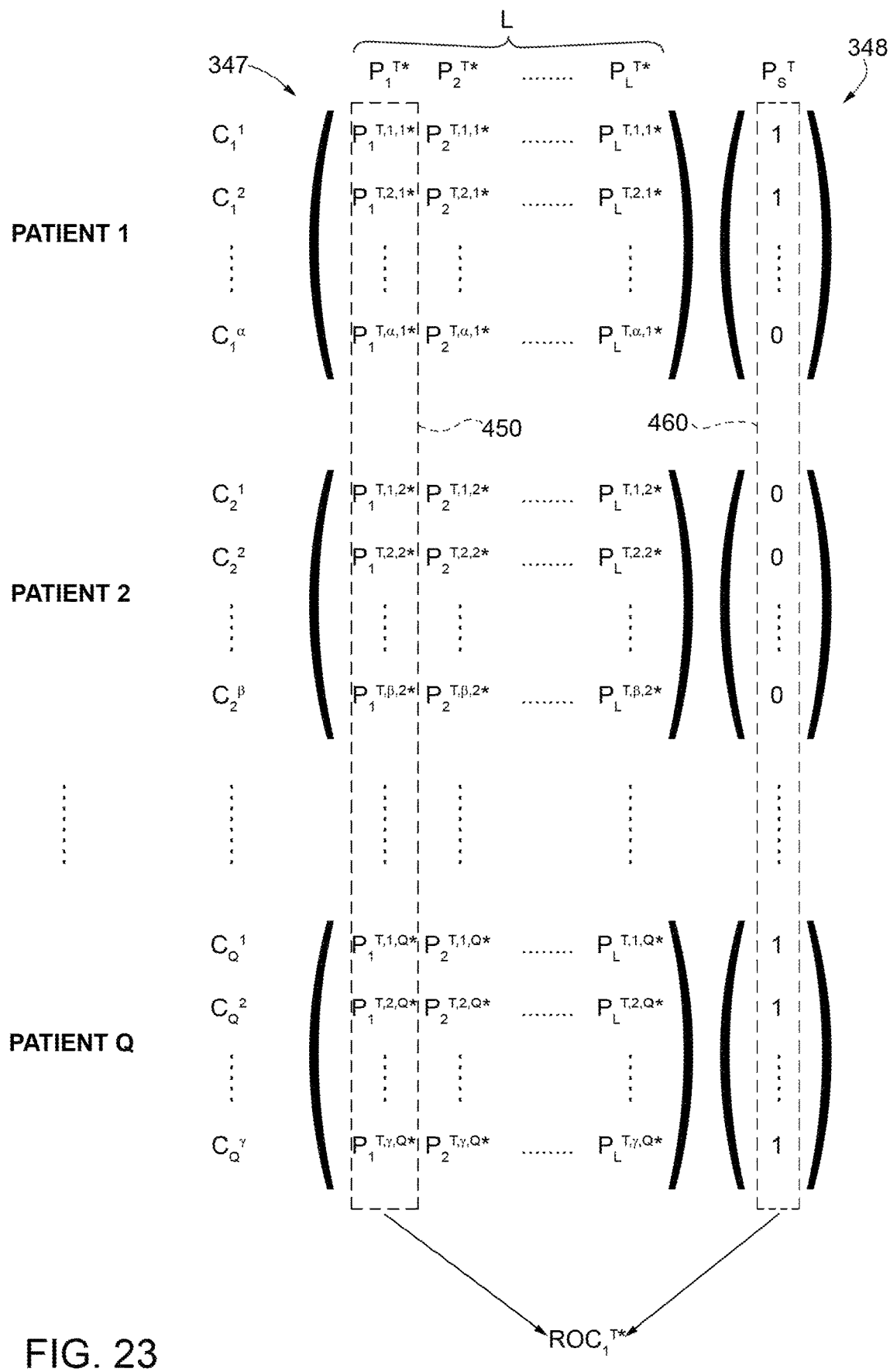
FIG. 23 shows matrixes of cell parameter values used during a further curve trend determination step performed by the present detection system.

Subsequently, the processing system 4 determines (block 181), for each of the cell parameters, a corresponding $ROC^{T*}$ cell curve and the relative area, in the same way as discussed with reference to block 62, without prejudice to the fact that the calculation is performed on the basis of a cell macrocolumn 450 (FIG. 23) given by the columns of the flat cell matrixes 347 which correspond to the cell parameter considered, and on the basis of a cell macrovector 460 given by the succession of the cell vectors 348 relative to the sample patients.

Figure 24:
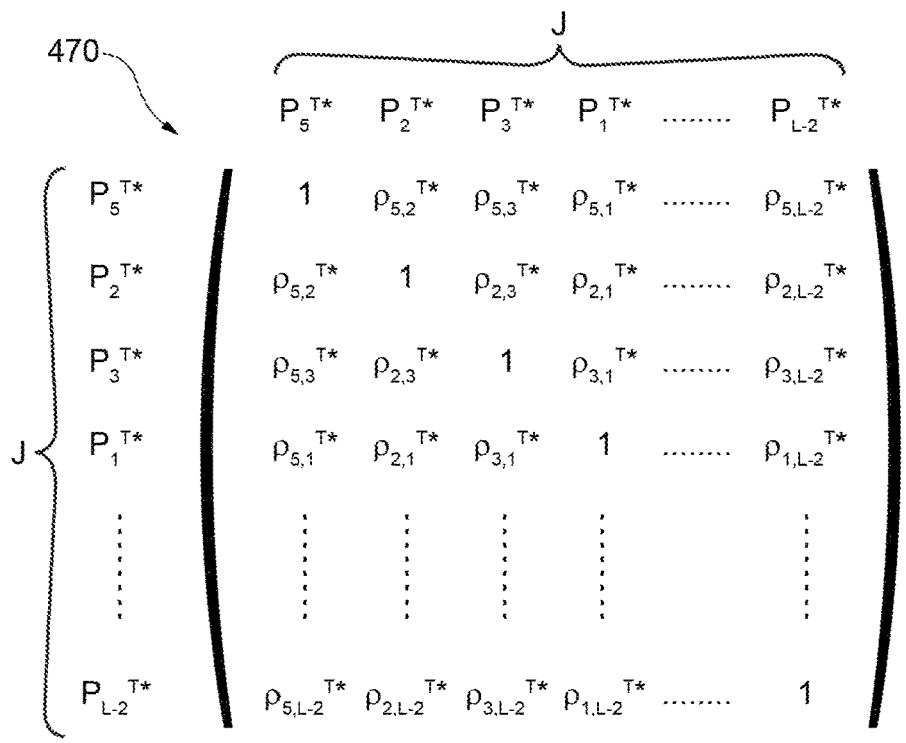

Subsequently, the processing system 4 determines (block 182) a cell correlation matrix (shown in FIG. 24, where it is indicated by 470), performing the same operations as those described for block 63, without prejudice to the fact that these operations are performed on the cell macrocolumns 450.

Subsequently, the processing system 4 selects (block 183) the significant cell parameters, based on the cell correlation matrix 470, performing the same operations as those described for block 64, without prejudice to the possibility of adopting a different threshold value from the one used in the operations in block 64.

Below it is assumed, for example, that the operations described so far result in choosing and storing a number A of significant cell parameters.

Figure 25:
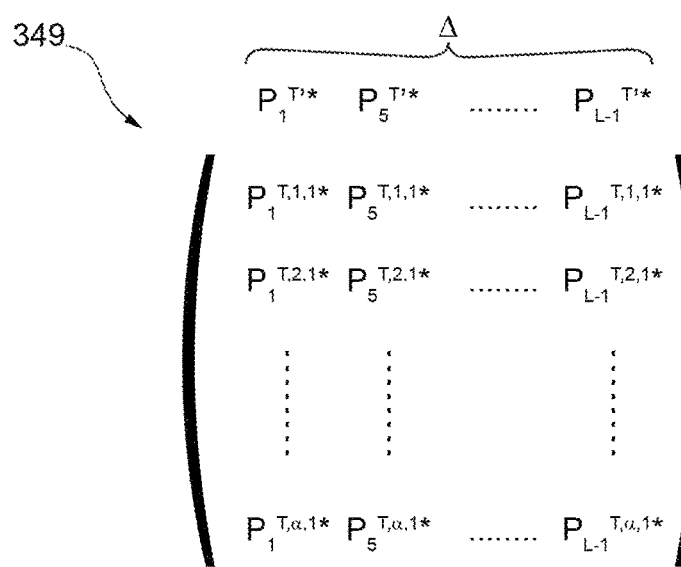

Again, with reference to FIG. 2C, the processing system 4 selects (block 176), from within the flat cell matrix 347 of each sample patient, only the columns relative to the significant cell parameters. In this way, a corresponding reduced cell matrix 349 is obtained, an example of which, relative to the first sample patient, is shown in FIG. 25, in which the significant cell parameters are indicated by the addition of a superscript.

Subsequently, the processing system 4 determines (block 177 of FIG. 2C) a third classifier (for example, of Bayes type, or decision tree or SVM), based on the values of the significant cell parameters $P_r^{T*}$ contained in the reduced cell matrixes 349 of the sample patients and of the corresponding binary indications $P_s^{T*}$. In particular, the processing system 4 generates and stores a mathematical model adapted to receive as input data the values of the cell parameters $P_r^{T*}$ of any one cell of any one patient and generate in output a corresponding indication of the degree of aggressiveness of the tumoral mass present in this cell.

Following the operating steps shown in FIGS. 2A-2C and applied to the sample patients, the processing system 4 has stored the first, the second and the third classifier, in addition to the list of the significant parameters, the significant regional parameters and the significant cell parameters. The CAD system 1 is therefore ready to be used on an unknown patient, or on a subject for which there is no information on the possible presence of tumoral masses.

Figure 26:
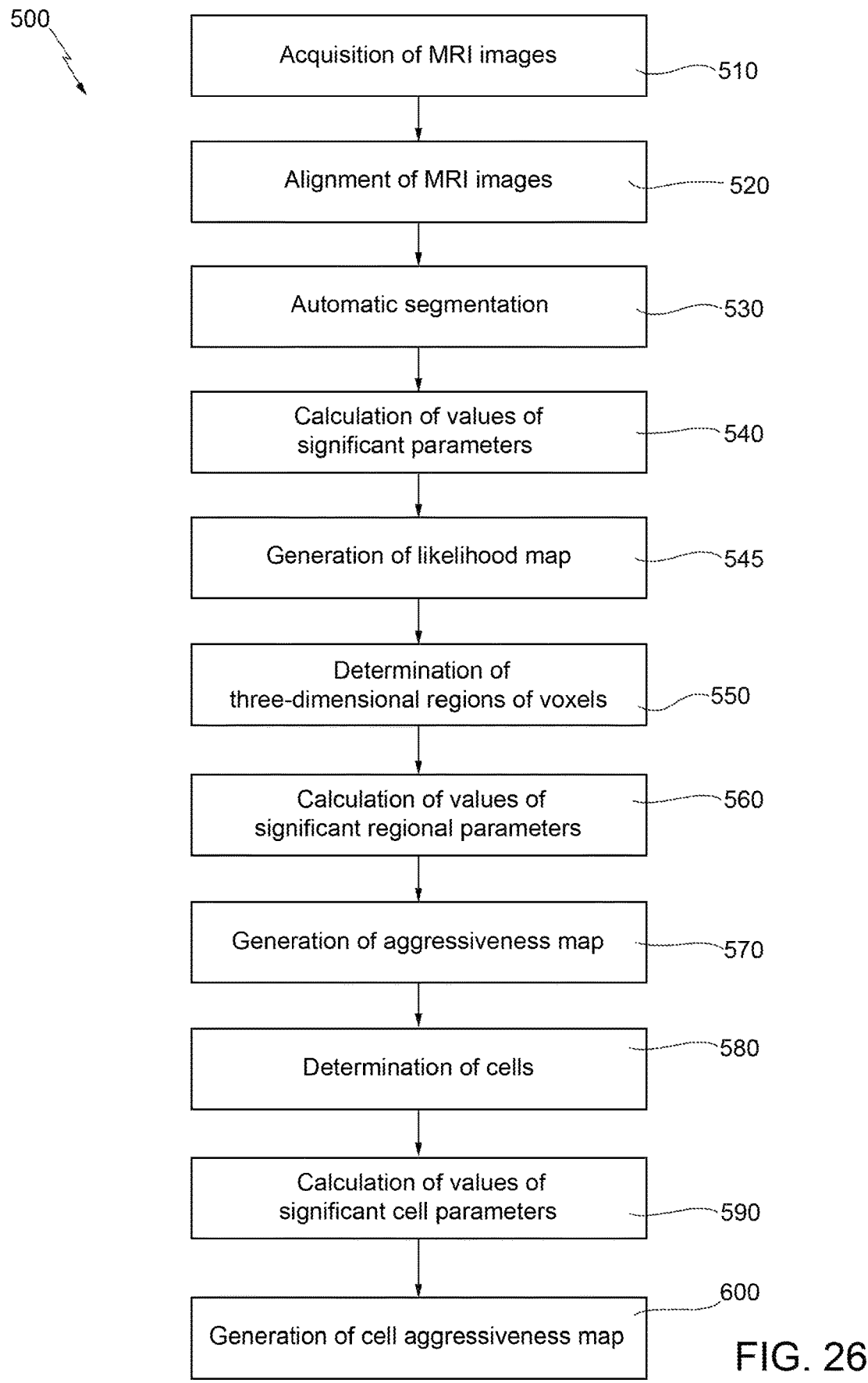
FIG. 26 shows a flow diagram relative to further operations carried out by the present detection system.

In particular, as shown in FIG. 26, the operations in blocks 10, 20 and 30 are performed, indicated here by 510, 520 and 530 respectively. Subsequently, the processing system 4 determines (block 540) the values of the significant parameters (the latter having been selected during the operations in block 60 of FIG. 2A) of the unknown patient.

Subsequently, the processing system 4 applies the first classifier to the values of the significant parameters of the unknown patient, generating (block 545) the three-dimensional likelihood map relative to the unknown patient.

The processing system 4 then performs the operations for the blocks 80, 90, 100, 110 and 120 (now indicated overall by 550), so as to determine the three-dimensional regions of voxels of the unknown patient.

Subsequently, the processing system 4 determines (block 560) the values of the significant regional parameters (namely, the regional parameters selected in block 150 of FIG. 2B) relative to the unknown patient.

The processing system 4 then applies the second classifier to the values of the significant regional parameters of the unknown patient, generating (block 570) an aggressiveness map relative to the unknown patient, which associates, with each three-dimensional region of voxels, a corresponding indication of the degree of aggressiveness.

Subsequently, the processing system 4 carries out the operations in blocks 171-172 (now indicated overall by 580), so as to determine the cells of the relevant three-dimensional regions of the unknown patient. In particular, the processing system 4 considers relevant the three-dimensional regions of voxels having degrees of aggressiveness higher, for example, than 3+3.

The processing system 4 then determines (block 590) the values of the significant cell parameters (namely, the regional cell parameters selected in block 175 of FIG. 2C) relative to the unknown patient.

The processing system 4 then applies the third classifier to the values of the significant cell parameters of the unknown patient, generating (block 600) a cell aggressiveness map relative to the unknown patient, which associates, with each cell of each relevant three-dimensional region of the unknown patient, a corresponding indication of the degree of aggressiveness.

The advantages offered by the present CAD system clearly emerge from the preceding description. In particular, the present CAD system allows identification and characterization of a prostate tumoral mass without the direct intervention of an expert. In fact, it is possible to identify a tumoral mass without the radiologist having to manually define the region of interest of the unknown patient, both in the identification step and in the step of characterization of the aggressiveness of the tumoral mass; this allows the reduction of human error in the reporting process.

In addition, selection of the significant parameters and the significant regional parameters results in increased computational efficiency.

Again, the present CAD system is able to select, without requiring the intervention of an expert, the three-dimensional regions having a high probability of including tumoral masses, and characterize their aggressiveness, on the basis of the corresponding values of the significant regional parameters.

Furthermore, the structural parameters and the regional parameters can be calculated also on small-dimension regions (for example, formed of only a few voxels); in particular, with reference to the regional parameters, this allows very precise indications to be provided on the aggressiveness and heterogeneity of a tumour, assisting the radiologist in the choice of the treatment most suited to the patient in question. In this regard, the division of the relevant three-dimensional regions into cells allows the precision level of the analysis to be further increased.

Lastly, it is clear that modifications and variations can be made to the present system without departing from the protective scope of the present invention, as defined in the attached claims. For example, said CAD system can be adapted to be used in body regions different from the prostate, such as, for example, breast, rectum and lungs.

Furthermore, the processing system 4 may be configured to generate further quantities, with respect to the preceding description. For example, the processing system 4 may generate, for each three-dimensional region of voxels of the unknown patient, a corresponding PIRADS (Prostate Imaging Reporting and Data System) score.

Lastly, the operations carried out by the present processing system 4 may differ from what is described. For example, the three-dimensional regions may be determined differently from what is described; for example, the processing system 4 may look for the absolute maximum and/or one or more relative maximums of each three-dimensional likelihood map and select the relative neighbourhoods, independently of the fact that these maximums exhibit probability values higher than a threshold. In this case, it is possible, for example, for each three-dimensional region to be formed of the voxels that are less than a predefined distance from a corresponding voxel that exhibits an absolute or relative maximum of probability.

It is furthermore possible for the step of determination of the three-dimensional regions to include an additional step with respect to what is described, in which a three-dimensional region is discarded if it does not meet a further criterion, for example relative to the form (for example, concavity/convexity).

The invention claimed is:

1. A computer-aided diagnosis (CAD) detection system (1) for detecting tumoral masses in an unknown tissue, that can be coupled to a magnetic resonance imaging (MRI) system (2) for receiving a number of unknown tissue scans, each scan comprising a corresponding plurality of MRI images ($F_i$) relating to a set of voxels (45), each voxel (51) being associated with a corresponding portion of the unknown tissue, the MRI images of each scan being indicative of values of at least a corresponding initial parameter; said CAD detection system comprising:
   a computer-based processing system (4) configured to determine, for each voxel, a number of corresponding values of first main parameters ($P_p'$), based on the MRI imaging;
   configured to determine, for each voxel, a corresponding probability value, based on the corresponding values of the first main parameters, said probability value being indicative of the probability that the corresponding portion of unknown tissue includes a corresponding tumoral portion;
   configured to select voxel groups ($R_{3D,1}$) based on:
   the probability values of the voxels, a probability threshold and a geometric criterion, so that each voxel group is formed by adjacent voxels, the probability values of which individually satisfy a predetermined relationship with the probability threshold, each voxel group also satisfying said geometric criterion; or
   the probability values of the voxels and a proximity criterion, so that each voxel group is formed by voxels adjacent to a corresponding relative or absolute probability maximum and satisfies said proximity criterion;
   configured to determine, for each voxel group, a plurality of corresponding values of second main parameters ($P_r^{T}$), each of said values of second main parameters being a function of the values of a corresponding initial parameter of the voxels of the group; and
   configured to determine, for each voxel group, a corresponding aggressiveness value of the group, based on the corresponding values of the second main parameters, said aggressiveness value of the group being indicative of the aggressiveness of the tumoral mass formed by the tumoral portions present in the corresponding portions of unknown tissue.

2. The CAD detection system (1) according to claim 1, wherein the computer-based processing system (4) is configured to select the voxel groups ($R_{3D,1}$) having group aggressiveness values greater than a group aggressiveness threshold;
   configured to determine, for each selected voxel group ($R_{3D,*}$), a plurality of corresponding cells (373) that form the selected voxel group;
   configured to determine, for each cell, a plurality of corresponding values of third main parameters ($P_r^{Ti*}$), each of said values of third main parameters being a function of the values of a corresponding initial parameter of the voxels of the cell; and
   configured to determine, for each cell, a corresponding aggressiveness value of the cell, based on the corresponding values of third main parameters, said cell aggressiveness value being indicative of the aggressiveness of the tumoral mass formed by the tumoral portions present in the corresponding portions of unknown tissue.

3. The CAD detection system (1) according to claim 2, wherein at least one of said second main parameters ($P_r^{T}$) is indicative of the homogeneity, or the contrast, or the entropy, or the energy, or statistical quantities of the values of the corresponding initial parameter, within each group of voxels ($R_{3D,1}$); and wherein at least one of said third main parameters ($P_r^{Ti*}$) is indicative of the homogeneity, or the contrast, or the entropy, or the energy, or statistical quantities of the values of the corresponding initial parameter, within each cell (373).

4. The CAD detection system (1) according to claim 1, wherein the computer-based processing system (4) is configured to determine, for each voxel (51), a corresponding value of at least a structural parameter, which is a function of the values of a corresponding initial parameter of voxels the arrangements of which, in respect to said voxel, satisfy a predetermined geometric condition; and wherein each first main parameter ($P_F'$) is alternatively equal to one of said initial parameters, or to one of said structural parameters.

5. The CAD detection system (1) according to claim 1, wherein the computer-based processing system (4) is configured to apply at least one classifier selected from: support vector machine classifiers, Bayes classifiers and decision tree classifiers.

6. The CAD detection system (1) according to claim 1, wherein said scans are based on at least a first type of imaging including: T2 weighted imaging, diffusion weighted imaging and dynamic contrast-enhanced magnetic resonance imaging.

7. A method for detecting tumoral masses in an unknown tissue, comprising the steps of:

providing a computer-aided diagnosis (CAD) detection system including a magnetic resonance imaging (MRI) apparatus (2) and a computer-based processing system (4);

receiving (510) a plurality of MRI images ($F_i$) from the MRI apparatus (2) relating to a number of unknown tissue scans, said MRI imaging being related to a set of voxels (45), each voxel (51) being associated with a corresponding portion of unknown tissue, the MRI images of each scan being further indicative of values of at least a corresponding initial parameter;

determining (540), for each voxel, a number of corresponding values of first main parameters ($P_P'$), based on the MRI imaging;

determining (545), for each voxel, a corresponding probability value, based on the corresponding values of the first main parameters, said probability value being indicative of the probability that the corresponding portion of unknown tissue includes a corresponding tumoral portion;

selecting (550) voxel groups ($R_{3D,1}$) based on:

the probability values of the voxels, a probability threshold and a geometric criterion, so that each voxel group is formed by adjacent voxels, the probability values of which individually satisfy a predetermined relationship with the probability threshold, each voxel group further satisfying said geometric criterion; or the probability values of the voxels and a proximity criterion, so that each voxel group is formed by voxels adjacent to a corresponding relative or absolute maximum of probability and satisfies said proximity criterion;

determining (560), for each voxel group, a plurality of corresponding values of second main parameters ($P_r^{T_1}$), each of said values of second main parameters being a function of the values of a corresponding initial parameter of the voxels of the group; and determining (570), for each voxel group, a corresponding group aggressiveness value, based on the corresponding values of second main parameters, said group aggressiveness value being indicative of the aggressiveness of the tumoral mass formed by tumoral portions present in the corresponding portions of unknown tissue.

8. The detection method according to claim 7, further comprising the steps of:

selecting (580) the voxel groups ($R_{3D,1}$) having group aggressiveness values greater than a group aggressiveness threshold;

determining (580), for each voxel group selected ($R_{3D}*$), a plurality of corresponding cells (373) which form the selected voxel group;

determining (590), for each cell, a plurality of corresponding values of third main parameters ($P_r^{T_1*}$), each of said values of third main parameters being a function of the values of a corresponding initial parameter of the voxels of the cell; and determining (600), for each cell, a corresponding cell aggressiveness value, based on the corresponding values of third main parameters, said cell aggressiveness value being indicative of the aggressiveness of the tumoral mass formed by the tumoral portions present in the corresponding portions of unknown tissue.

9. The detection method according to claim 8, wherein at least one of said second main parameters ($P_r^{T_1}$) is indicative of the homogeneity, or the contrast, or the entropy, or the energy, or statistical quantities of the values of the corresponding initial parameter, within each voxel group ($R_{3D,1}$); and wherein at least one of said third main parameters ($P_r^{T_1*}$) is indicative of the homogeneity, or the contrast, or the entropy, or the energy, or the statistical quantities of the values of the corresponding initial parameter, within each cell (373).

10. The detection method according to claim 7, further comprising the step of determining (40), for each voxel, a corresponding value of at least a structural parameter, which is the function of the values of a corresponding initial parameter of voxels the arrangements of which, in respect to said voxel (51), satisfy a predetermined geometric condition; and wherein each first main parameter ($P_P'$) is alternatively equal to one of said initial parameters, or to one of said structural parameters.

11. A method for determining an aggressiveness classifier of tumoral areas, comprising the steps of:

for each known tissue of a plurality of known tissues, receiving (10) a number of known tissue scans, each scan comprising a corresponding plurality of MRI images ($F_i$) relating to a set of voxels (45) of the known tissue, each voxel (51) being associated with a corresponding portion of the known tissue, the MRI images of each scan being indicative of values of at least a corresponding initial parameter;

determining (50), for each voxel of each known tissue, a number of corresponding values of first candidate parameters ($P_P$), based on the MRI images of the known tissue, said first candidate parameters including said initial parameters;

storing, for each voxel of each known tissue, a corresponding binary indication relating to the presence/absence of a tumoral portion in the corresponding portion of known tissue; and selecting (60) a subset of first candidate parameters, based on the values of first candidate parameters of voxels of the known tissues and of the corresponding binary indications of the presence/absence of tumoral portions;

determining (70) a first classifier, based on the values of first candidate parameters selected ($P_P'$) of the voxels of the known tissues and the corresponding binary indications of the presence/absence of tumoral portions;

applying (70), for each voxel of each known tissue, said first classifier to the corresponding values of first candidate parameters selected ($P_P'$), so as to determine a corresponding probability value, which is indicative of the probability that the corresponding portion of known tissue includes a corresponding tumoral portion;

selecting (80, 90, 100, 110, 120), for each known tissue, corresponding voxel groups ($R_{3D,1}$) based on:

the probability values of the voxels, of a predetermined threshold and of a geometric criterion, so that each voxel group is formed by adjacent voxels, the probability values of which individually satisfy a predetermined relationship with the probability threshold, each voxel group also satisfying said geometric criterion; or the probability values of the voxels and a proximity criterion, so that each voxel group is formed by voxels adjacent to a corresponding relative or absolute maximum of probability and satisfies said proximity criterion;

determining (130), for each voxel group of each known tissue, a plurality of corresponding values of candidate regional parameters ($P_r^T$), each of said values of candidate regional parameters being a function of the values of a corresponding initial parameter of the voxels of the group; and storing, for each voxel group of each known tissue, a corresponding binary indication relating to the aggressiveness of the tumoral portions present in the corresponding portions of known tissue; and selecting (150) a subset of candidate regional parameters ($P_r^T$), based on the values of the candidate regional parameters of the voxel groups of the known tissues and of the corresponding binary aggressiveness indications;

determining (170) a second classifier, based on the values of the candidate regional parameters selected ($P_r^T$) of the voxel groups of the known tissues and the corresponding binary indications relating to the aggressiveness.

12. The method according to claim 11, wherein said step of selecting (60) a subset of first candidate parameters ($P_P$) comprises carrying out operations for discarding first candidate parameters, each first candidate parameter discarded having a respective correlation with at least another first candidate parameter that exceeds a first correlation threshold; and wherein said step of selecting (150) a subset of candidate regional parameters ($P_r^T$) comprises carrying out operations for discarding candidate regional parameters, each candidate regional parameter discarded having a respective correlation with at least another candidate regional parameter that exceeds a second correlation threshold.

13. The method according to claim 11, further comprising the steps of:

selecting (171), for each known tissue, the voxel groups ($R_{3D}^*$) having binary indications of aggressiveness equal to a predetermined binary value;

determining (172), for each voxel group selected, a plurality of corresponding cells (373) that form the voxel group selected;

determining (173), for each cell, a plurality of corresponding values of candidate cell parameters ($P_r^{T*}$), each of said values of candidate cell parameters being a function of the values of a corresponding initial parameter of the voxels of the cell; and storing, for each cell, a corresponding binary indication relating to the aggressiveness of a tumoral portion in the corresponding portion of known tissue; and selecting (175) a subset of candidate cell parameters ($P_r^{T*}$), based on the values of candidate cell parameters of the cells of known tissues and of the corresponding binary aggressiveness indications;

determining (177) a third classifier, based on the values of the selected candidate cell parameters of the cells of known tissues and of the corresponding binary indications relating to the aggressiveness.

14. The method according to claim 13, wherein said step of selecting (175) a subset of candidate cell parameters ($P_r^{T*}$) comprises carrying out operations for discarding candidate regional parameters ($P_r^{T*}$), each candidate cell parameter discarded having a respective correlation with at least another candidate cell parameter that exceeds a third correlation threshold.

* * * * *